US 8,565,870 B2

(12) United States Patent
Malackowski et al.

(10) Patent No.: US 8,565,870 B2
(45) Date of Patent: Oct. 22, 2013

(54) SYSTEM OF IMPLANTABLE MEDICAL DEVICES INCLUDING A PLURALITY OF SPACED APART DEVICES AND A COMMON BUS OVER WHICH POWER AND OPERATING INSTRUCTIONS ARE DISTRIBUTED TO THE DEVICES

(71) Applicant: Stryker Corporation, Kalamazoo, MI (US)

(72) Inventors: Donald W. Malackowski, Schoolcraft, MI (US); John J. Janik, Hudsonville, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 13/657,938

(22) Filed: Oct. 23, 2012

(65) Prior Publication Data

US 2013/0066180 A1 Mar. 14, 2013

Related U.S. Application Data

(63) Continuation of application No. PCT/US2011/034416, filed on Apr. 29, 2011.

(60) Provisional application No. 61/329,844, filed on Apr. 30, 2010.

(51) Int. Cl.
*A61N 1/00* (2006.01)
*A61B 5/04* (2006.01)
*A61B 5/02* (2006.01)

(52) U.S. Cl.
USPC ............. 607/4; 600/372; 600/377; 600/508; 607/9; 607/116; 607/119

(58) Field of Classification Search
USPC ................ 600/372–375, 377, 393, 508–509; 607/4–5, 9–15, 115–116, 118
See application file for complete search history.

(56) References Cited

U.S. PATENT DOCUMENTS

| 6,970,742 | B2 * | 11/2005 | Mann et al. ................. 607/23 |
| 7,627,376 | B2 * | 12/2009 | Dennis et al. ............... 607/36 |
| 7,682,316 | B2 * | 3/2010 | Anderson et al. ........... 600/528 |
| 2005/0033372 | A1 | 2/2005 | Gerber |
| 2005/0267549 | A1 | 12/2005 | Della Santina et al. |
| 2006/0030918 | A1 | 2/2006 | Chinn et al. |

(Continued)

FOREIGN PATENT DOCUMENTS

| EP | 1862196 A2 * | 12/2007 |
| WO | 2008/039982 A2 | 4/2008 |
| WO | 2009/111142 A2 | 9/2009 |

OTHER PUBLICATIONS

European Patent Office, "ISA Search Report and Written Opinion for PCT/U52010/034416", Jul. 6, 2011.

*Primary Examiner* — Linda Dvorak
*Assistant Examiner* — Brian M Antiskay

(57) ABSTRACT

A system implantable components (32, 36, 38, 40) for providing therapy to or monitoring the physiologic state of living tissue. The components exchange signals over implanted bus (34). The bus includes a trunk (84) and at least one branch (14) The at least one branch is connected to and able to move relative to the trunk. Signals are inductively exchanged between the branch and the one or more trunks.

19 Claims, 18 Drawing Sheets

(56) References Cited

U.S. PATENT DOCUMENTS

| | | |
|---|---|---|
| 2006/0058627 A1 | 3/2006 | Flaherty et al. |
| 2006/0122660 A1 | 6/2006 | Bov et al. |
| 2006/0253170 A1* | 11/2006 | Wyler et al. .................... 607/49 |
| 2008/0140139 A1 | 6/2008 | Heinrich et al. |
| 2010/0063568 A1 | 3/2010 | Staunton et al. |
| 2011/0034977 A1 | 2/2011 | Janik et al. |

* cited by examiner

SYSTEM OF IMPLANTABLE MEDICAL DEVICES INCLUDING A PLURALITY OF SPACED APART DEVICES AND A COMMON BUS OVER WHICH POWER AND OPERATING INSTRUCTIONS ARE DISTRIBUTED TO THE DEVICES

RELATIONSHIP TO EARLIER FILED APPLICATIONS

This application is a continuation of PCT Pat. App. No. PCT/2011/034416 filed 29 Apr. 2011. PCT Pat. App. No. is a non-provisional of U.S. Pat. App. No. 61/329,844 filed 20 Apr. 2010. The contents of the above-identified priority applications are incorporated by reference into this application.

FIELD OF THE INVENTION

This invention relates generally to an implantable electrode array assembly and, more particularly, to a system for powering and regulating the operation of plural electrode array assemblies implanted into a living being.

BACKGROUND OF THE INVENTION

There are a number of medical conditions for which an effective therapy is driving current through a section of the tissue of a patient. Often the current is driven between electrodes of an electrode array implanted in the patient. Generally, the electrode array includes a non-conductive carrier on which typically two or more electrodes are disposed. Once the array is implanted, current is driven from at least one of the electrodes, through the adjacent tissue, to at least one of the other electrodes. The current flow through the tissue influences the tissue to accomplish a desired therapeutic result. For example, an electrode array positioned adjacent the heart may flow currents to stimulate the appropriate contraction and expansion of the heart muscles.

Current is also flowed from implanting electrode arrays into adjacent neural tissue to induce a desired neurological or physical effect. In one application, the current driven between the electrodes of an array placed on top of the dura in the vertebral column reduces the extent to which chronic pain signals are perceived by the brain. Alternatively, the array may be placed in a location where the current flow stimulates a feeling of satiation as part of an appetite suppression/weight management therapy. In another application, the current is flowed to tissue or nerves associated with the bladder or the anal sphincter to assist in control of incontinence. Electrodes may be implanted in a paralysis victim to provide muscle control and/or a sense of feeling.

The Applicants' Patent Application No. PCT/2009/33769, FOLDABLE, IMPLANTABLE ELECTRODE ARRAY ASSEMBLY AND TOOL FOR IMPLANTING SAME, published as WO 2009/111142, and IMPLANTABLE ELECTRODE ARRAY ASSEMBLY INCLUDING A CARRIER FOR SUPPORTING THE ELECTRODES AND CONTROL MODULES FOR REGULATING OPERATION OF THE ELECTRODES EMBEDDED IN THE CARRIER, AND METHOD OF MAKING SAME, filed 5 Aug. 2009 the contents of which are published as US Pat. Pub. No. 2011/0034977 A1, the contents of both of which are explicitly incorporated herein by reference, each describe an electrode array that includes a carrier on which plural electrodes are arranged in a row by column matrix. An advantage of this type of array is that it allows current to be flowed between numerous different combinations of electrodes. Depending on which electrodes are connected to associated current sources and sinks, this array can be operated so that there are two or more current flows occurring simultaneously between different sets of electrodes. Once this assembly is deployed, the practitioner can initially drive current between different combinations of electrodes. Current therefore flows through different sections of tissue. This allows the practitioner to determine between which electrodes, through which tissue, the current flow offers the greatest benefit and/or tolerable side effects. Once the optimal current flow path between the electrodes is determined, the array and its associated power supply are set to operate in this state.

In comparison to other electrode arrays with lesser numbers of electrodes, the above-described array makes it possible to flow current through more sections of tissue and to selectively focus/diffuse the current flow. In contrast to an electrode array with a smaller number of electrodes, use of the above-described array increases the likelihood that the current flow can be set to provide desired therapeutic effects, with tolerable side effects. Thus, this electrode array increases the likelihood that the flowing of current through the tissue of a patient can serve as effective therapy for certain medical conditions. cribed electrode array make it possible increase There are, however, limits to which the extent that a single electrode array can function as a useful therapeutic medical device. In particular, there are many situations where an individual may benefit by having current simultaneously flowed through different spaced tissue that are spaced apart 5 cm or more. For example, an individual may be suffering from the sension chronic pain in both the lower leg and upper arm. Presently, this medical condition would be treated by implanting into the a single implantable pulse generator and two spaced apart percutaneously implanted octrode (1×8) arrays, One octrode array would typically placed against the spine at level T8-T10 (lower leg). The second octrode array is placed against the spine at level C5-T1 (arm). At best, each octrode array is limited in the size and number of sections of tissue through which it can flow current. This means the ability of the array itself to provide pain relief is limited.

As an alternative, one could potentially place a single electrode against the upper extremity to attempt to treat the pain peripherally. Unfortunately, this may not provide satisfactory relief. One reason that, for the array electrodes to flow current through the tissues that would result in the desired therapy, the array would most likely have to extend over several internal joints. The repetitive stress and motion the array would undergo in this placement process would expose the array to a significant risk of prior to deployment, fracture. Also it may be difficult to place the array using the presently available delivery tools.

To mask the transmission of these pain signals, it may be necessary to simultaneously flow current through sections of the spinal cord spaced apart 5 cm or more. Present manufacturing restraints make it difficult to provide a single electrode that can be deployed over these widely spaced apart sections of tissue. Medically it may be difficult to precisely position an array so the spaced apart sections of the array itself are positioned over the tissue through which the current flows will offer the desired therapeutic effect. Even when it is possible to both provide and position such an array, there may be reasons why such a device has minimal utility. For example, if the array shifts position, the electrodes may not cover a section of targeted tissue through which the current flow will provide a therapeutic effect.

Also, it should be appreciated that, when simultaneously sourcing current through separate sections of tissue, it may be desirable to do so using electrodes that have different physical structures. This may be necessary if, in the same patient, it is necessary to provide treatment for both chronic pain and the side effects of Parkinson's disease. For example, in the spinal cord it may be desirable to implant an array designed to extend both arcuately and longitudinally over a section of the spinal column. Simultaneously, a ring electrode may be implanted in the basil ganglia to provide omnidirectional stimulation in the treatment of Parkinson's side effects.

The present common practice is to connect each of these different arrays with its own implantable pulse generator (IPG). Each IDC applies the current directly to specific on-array electrodes.

Thus, the present practice is to, when implanting plural electrode arrays in a patient, often implant plural IPGs. Typically, to implant an IPG, an incision is made into the patient to create a subcutaneous pocket for holding the IPG. Implanting plural IPGs increases the surgical trauma to which a patient is exposed in order to obtain the benefit of the plural electrode arrays.

There have been proposals to implant into a patient a single control unit capable of powering and controlling the current out put by multiple spaced apart electrode arrays. One proposal has been to have this single control unit wirelessly transmit signals to the electrode arrays implanted in various locations throughout the body. To date, this has proved technically difficult to execute. Another proposal would be to simply connect each electrode array to this common control unit by its own set of wires. This implant would make it necessary to string numerous wires through the body of the patient. These wires would extend from a single location, the control unit. As the individual in whom these devices are implanted moves, the tissue and organs internal to the person also moves. Over time, the movement of the tissue and organs surrounding the wires can displace the wires. The individual sets of wires could eventually start to cross each other. Once this happens, there is the possibility that the movement of one set of wires results in the displacement of a second set of wires. This movement of the second set of wires could cause these wires to disconnect from the array to which they are connected. Alternatively, the movement of the second set of wires can cause the like displacement of the attached array. The array movement can result in its electrodes shifting position so that they are no longer disposed against the tissue through which current flow offers therapeutic benefit. Should the array be repositioned to this extent, it no longer functions for the purpose for which it is implanted.

SUMMARY OF THE INVENTION

This invention relates to a new and useful system for providing power and control signals to an electrode array. More specifically, this invention relates to a system for providing power and control signals to plural spaced apart electrode arrays.

The system of this invention includes at least one implantable device controller (IDC) and a plurality of spaced apart electrode arrays. The IDC generates the power used to energize the current sources and current sinks integral with each electrode array. The IDC broadcasts commands to the individual electrode arrays that indicate over which electrodes the current is to be source from and sunk back into. These commands also indicate the levels of the current to be sunk/sourced through the electrode. A common bus connects the individual arrays to the IDC.

In some versions of the invention, system may include devices other than arrays with electrodes through which current is sourced/sunk. These other devices are sensors capable of measuring physiological parameters indicative of specific states of the condition of the patient.

In some versions of the invention, the bus of this invention is a two wire bus. A bus trunk extends from the IDC. A bus branch extends from each array or other device also part of the system. A sleeve-like cuff is attached to the free end of each bus branch. A coil, connected to the bus branch wires, is disposed in the cuff. The cuff is designed with a through bore dimensioned to allow the cuff to closely fit over and slide over the bus trunk.

In this version of the invention, the IDC transmits AC signals over the bus trunk. The signals are transferred by inductive coupling through the bus trunk wire to the coils contained in the individual cuffs. The signals that develop across the cuff coils are applied by the bus branches to the electrode arrays to which the branches are connected.

Integral with each array is a power harvesting circuit. The power harvesting circuit stores the power contained within the received signals. The stored power is used to energize the current sources and/or sinks integral with the array.

The signals transmitted by the IDC do more than power the electrode arrays. Integral with these signals are commands that control operation of the electrode arrays. Each command includes identification data. These data indicate the specific component integral with an array or other system device that is to act on the command. Most commands also include one or more operands. The operands are the data indicating the instruction the component is to execute.

Integral with most electrode arrays is at least one demodulator and at least one control processor. The demodulator demodulates the signals transmitted by the IDC to extract the commands. The commands are forwarded to the control processor. The control processor determines if a received command is for an array component under control of the processor. If the signals are for a particular component under control of that processor, the processor generates instructions to that specific component to operate in accordance with the received command.

In some versions of the invention, the IDC does more than generate power signals and commands to the different arrays. The IDC also receives information-containing signals from the arrays and/or other devices. Information sent by these devices may include data describing the voltage measured at a particular electrode integral with the array. The information may also indicate the status of a component integral with the array. This type of information, for example, are data regarding the operating state about a particular current source or sink on the array.

Based on the data received from the electrode arrays and other system devices, the IDC processor generates updated commands to the arrays. For example, the received data can indicate that, at one electrode, a relatively high voltage is present. These data may be interrupted by the IDC as an indication that the patient is receiving indications of pain when there may be no physiological reasons for those pain signals to be transmitted. In response to receipt of this information, the IDC processor may transmit commands to current sources/sinks on a second array to increase the current flow through the patient at a location different from where the pain signals are originating. This action would then block the transmission of the chronic pain signals to the brain.

Another feature of this invention is that the signals exchanged between the implantable device controller and the plural electrode arrays are exchanged over a common set of conductors, the wires forming the bus trunk. This minimizes the number of wires implanted in the patient. Still another feature of this invention is that the cuffs integrally with the bus branch coils move relative to the bus trunk. In the event that either the bus trunk of one of the bus branches is displaced, the associated coil can move over the bus trunk. This ensures that the coils remain connected to the bus trunk to facilitate the exchange of signals between the implantable device controller and the system devices.

BRIEF DESCRIPTION OF THE DRAWINGS

The invention is pointed out with particularity in the claims. The above and further features and benefits of this invention are set following in the following Detailed Description taken in conjunction with the accompanying drawings in which:

DETAILED DESCRIPTION

Figure 1:
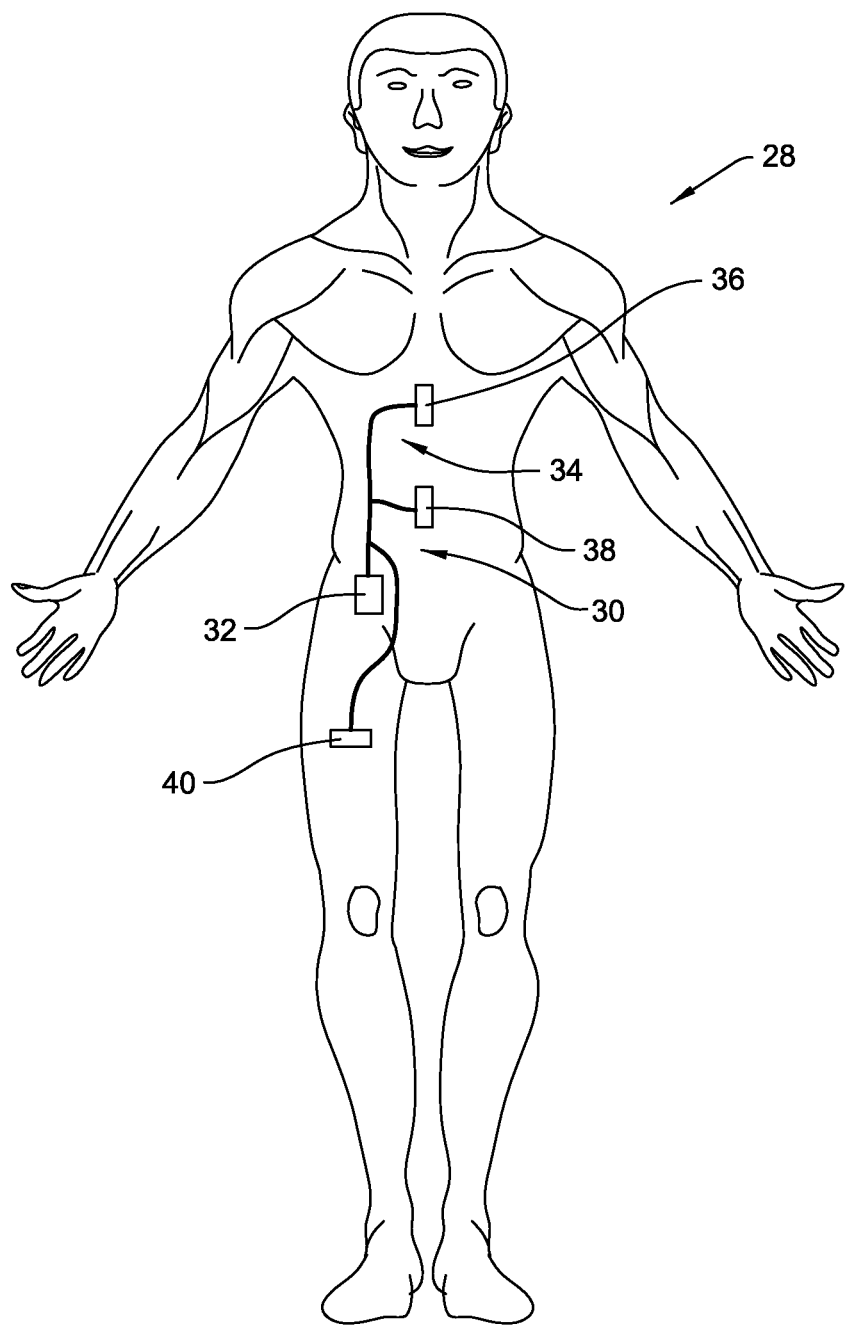
FIG. 1 is view of a living being, a human, with the electrode array system of this invention implanted therein.

FIG. 1 illustrates a living being, a human, 28, into which the electrode array system 30 of this invention is implanted. System 30 includes an implantable device controller (IDC) 32. A bus 34 extends from the IDC 32. A number of electrode arrays 36, 38 and 40 are connected to the IDC 32 over bus 34.

As discussed below, each electrode array 36, 38, and 40 includes a number of electrodes. Each electrode array 36 and 38 includes one or more current sources and/or sinks. The IDC 32 generates signals that power the arrays 36, 38 and 40. The IDC 32 also generates commands to the electrode arrays 36, 38 and 40. Based on the received command signals, one or more drive modules internal to each electrode array 36 and 38 causes each current source/sink to source/sink a certain amount of current. Also, based on the command signals, the control module causes the current to be source/sunk through specific ones of the electrodes integral with the array.

Electrode array 40 does not include current sources/sinks. Electrode array 40 includes signal processing circuits that monitoring the voltages measured across the electrodes integral with the array. A transponder integral with electrode array 40 generates messages containing data describing the voltages measured by the electrodes. These messages are output over bus 34 to the IDC 32. Based on the data received from the electrode array 40, the IDC 32 updates the commands regarding through which electrodes the current should be sourced/sunk and the magnitude of the current to be flowed through the surrounding tissue.

Figure 2:
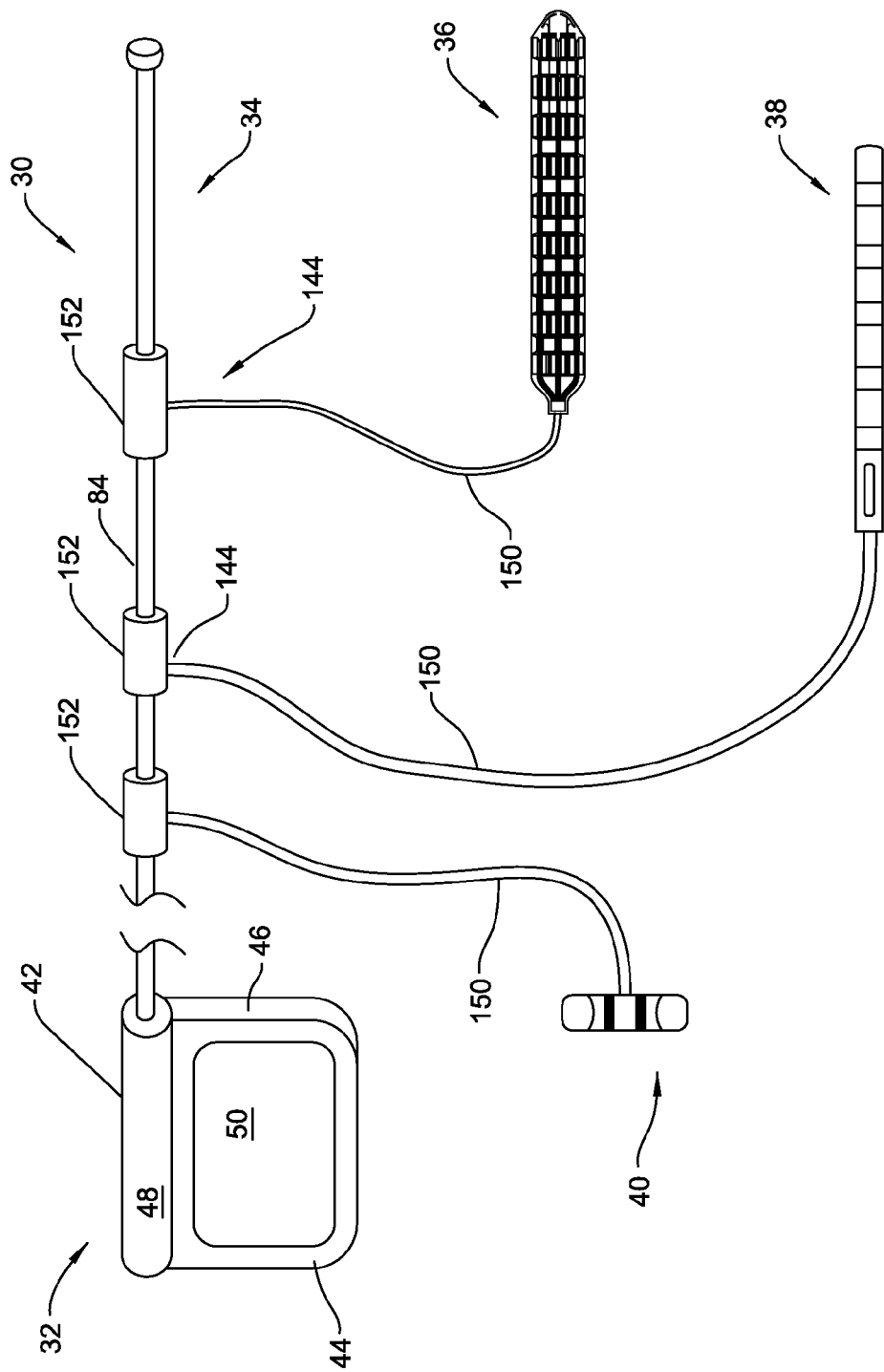
FIG. 2 illustrates how the basic components of the system of this invention are connected together to form the system.

As seen in FIG. 2, the IDC 32 includes a shell 42. Shell 42 is formed from a biocompatible metal such as titanium or a biocompatible plastic such as a silicone plastic. In the illustrated version of the invention, shell 42 is generally in the form of a polyhedron with rounded corners. There are two major faces 44, one seen in FIG. 2, that are spaced apart by side panels 46 (one shown) and a bottom panel (not illustrated) smaller in width. While shell 42 is generally poyhedronal in shape, the shell is shaped to have a cylindrical head 48 that extends along the top of the shell, between the major faces 44. Head 48 is opposite the end of the shell across which the bottom panel extends. In the event shell 42 is formed out of metal, a panel 50 is seated in an opening (not identified) formed in one of the shell major faces 44. Panel 50 is formed from a biocompatible plastic such as silicone plastic or a ceramic such as low-temperature cofired ceramic.

Figure 3:
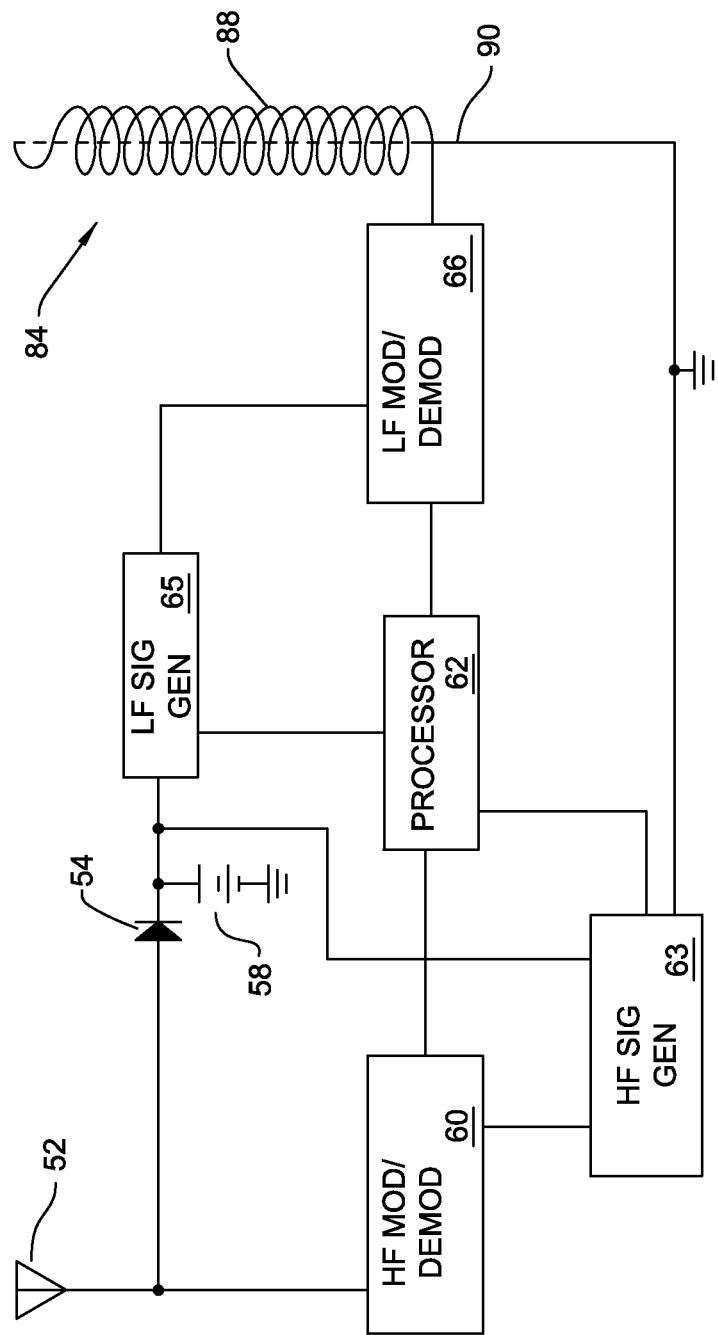
FIG. 3 is a block diagram of the components internal to the implantable device controller of this invention.

As seen in FIG. 3, internal to the IDC shell 42 is a coil 52, schematically depicted as an antenna. If shell 42 is formed from plastic, coil 52 is disposed against the inner surface of or embedded in a section forming one of the major faces 44. If shell 42 is formed from metal, coil 52 is embedded disposed against the internal face of panel 50. Coil 52 is structured to receive signals from the coil associated with a complementary external device controller (not illustrated). In some versions of the invention, the external device controller and coil 52 exchange signals at a frequency in the range of 1 to 5 MHz The signals received by coil 52 are forwarded to a power harvesting circuit. In FIG. 3, the power harvesting circuit is represented by a diode 54, and a rechargeable cell 58. The anode of diode 54 is tied to coil 52. The cathode of the diode 54 is tied to the rechargeable cell 58. Diode 54 rectifies the signal that is developed across coil 52. The power contained within the rectified signal is stored in cell 58. The charge stored in cell 58 is applied to the other components internal to the IDC 32. In FIG. 3, cell 58 is shown as sourcing power to two components, a high frequency signal generator 63 and a low frequency signal AC generator 65. This is for ease of illustration only. It should be appreciated the charge stored by cell 58 is used to energize the other components internal to the IDC 32. Also, while not illustrated, it should also be understood that the power harvesting circuit includes a voltage regulator. The voltage regulator ensures that the power signal(s) output by the cell 52 is (are) output to the other IDC components at the appropriate voltage level(s).

Another component internal to the IDC 32 is a high frequency (HF) modulator/demodulator 60. The signals developed across coil 52 are applied to the HF modulator/demodulator 60. The HF modulator/demodulator 60 extracts the data signals embedded in the signals developed across coil 52. These signals are applied to a processor 62 also part of the IDC 32.

High frequency signal generator 63 is also disposed inside the IDC shell 42. HF signal generator 63 generates a signal that is applied to coil 52 for reception by the external device controller. The signal output by the HF signal generator 63 as at the frequency at which the external device controller applies signals to coil 52. The signal output by the HF signal generator is applied to the HF modulator/demodulator 60. The modulator/demodulator 60 includes components able to module the HF signal so that signal applied by the coil contains data signals. In some versions of the invention, the modulation process is employed is a phase shift modulation or frequency shift modulation.

In FIG. 3 the high frequency signal generator 63 is shown tied to ground. The only other component in FIG. 3 tied to ground is return wire 90 of bus trunk 84. This is for ease of illustration only. The other circuits internal to the IDC 32 may likewise, if appropriate, be tied to ground.

Processor 62 regulates the operation of the individual electrode arrays 36, 38 and 40. This control is based, in part on preprogrammed operating instructions stored in memory 75 (FIG. 3B) integral to the processor 62. Alternatively, memory 75, or portions thereof, are a separate component of the IDC also disposed in shell 42. The processor 62 also capable of generating commands based on new instructions received post-implantation, over coil 52. The processor 62 is also capable of receiving data from the electrode arrays 36, 38 and 40. These data include information regarding the voltage present at specific electrodes or other signals representative of the state of the patient. These data also include information regarding the operating states of components. Based on these data, processor 62 further adjusts the operation of electrode arrays 36 and 38.

The IDC 32 also includes a low frequency (LF) signal generator 65. Low frequency signal generator 65 generates a signal at frequency somewhere between 5 kHz and 500 kHz. The signals generated by low frequency signal generator are applied to a low frequency (LF) modulator/demodulator 66. The LF modulator/demodulator 66 also receives the command signals output by processor 62. Based on the commands received from processor 62, the LF modulator/demodulator 65 modulates the signals from the LF generator. The signals may be modulated using phase shift or amplitude modulation. The modulated signals are output over a bus trunk 84 that extends from the IDC shell 42.

Figure 3A:
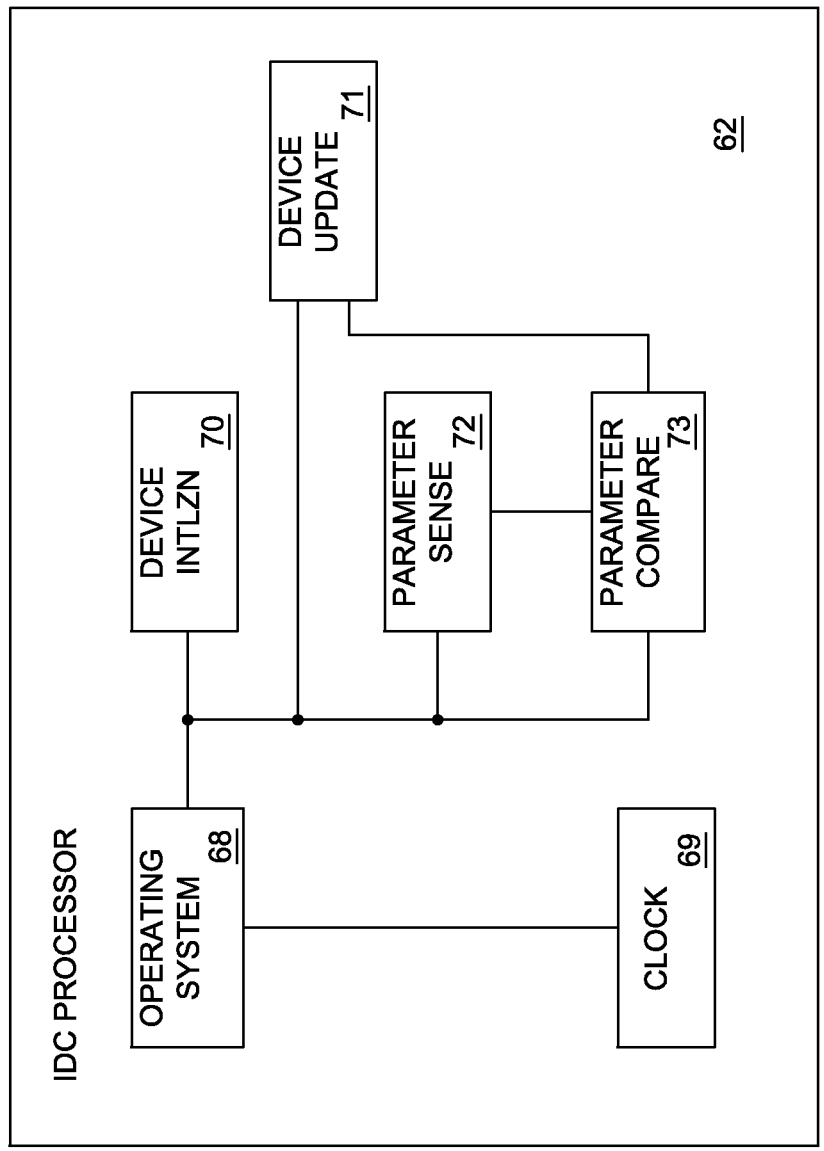
FIG. 3A is a block diagram of software modules that are run on the processor internal to the implantable device controller.

FIG. 3A depicts software modules executed by IDC processor 62. One of these modules is the processor's own operating system 68. Operating system 68 controls the overall operation of the processor 62. Part of the function of the operating system module 68 is to read data into and out of the other software modules that are run on the processor 62. Operating system 68 contains the instructions required to read data into and out of the processor through modulator/demodulators 60 and 66. A clock module 69 maintains a system time. The time maintained by clock module 69 is regulates operation of components internal to the IDC 32 as well as components internal to arrays 36, 38 and 40.

A device initialization module 70 is also run by the IDC processor 62. Upon start-up of the system 30, device initialization module 70 sets the initial operating states of the components integral with the system arrays 36, 38 and 40. As discussed below, once the system 30 is initialized, it may be necessary to reset the operating states of the array components. The resetting of the operating of these components is based on commands generated by a device update module 71.

The IDC processor 62 also periodically executes both a parameter sense module 72 and a parameter compare module 73. The parameter sense module 72 processes data received from the sensing components integral with the devices from which the IDC receives sensor signals. This processing may include the filtering of the data and/or a generation of a frequency/current plot for the data over a select range of frequencies. The data generated by the parameter sense module is applied to the parameter compare module. The parameter compare module 73 compares the processed sensor signals to target values. For example, the voltage over time for the voltages representative of pain signals at a location rostral to where the therapy signal are applied may be compared to the target value by a least squares regression method.

The comparison data generated by the parameter compare module 73 representative of the comparisons is applied to the device update module 71. Based on the comparison data, the device update module 71 generates commands that cause the resetting of the array components. These commands are then output over bus 32 by the IDC processor operating system sense module 68.

Figures 3B, 3C:
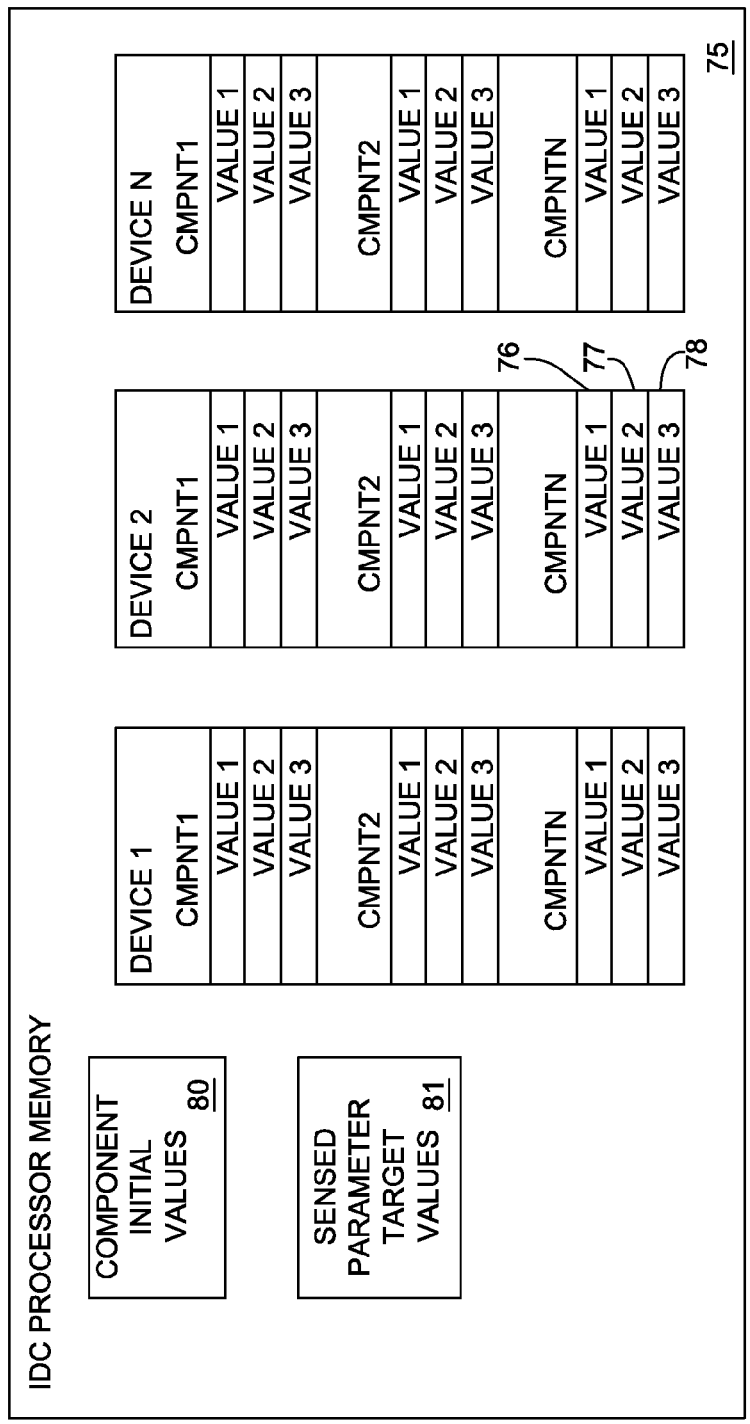
FIG. 3B is a block diagram of the contents of the memory integral with the implantable device controller processor.
FIG. 3C is a block diagram of how a value field in the IDC memory may include plural sub-fields.

The memory 75 connected to the IDC processor 62 is illustrated by FIG. 3B. While not illustrated, memory 75 contains the instructions forming the above-described software modules run on processor 63 described with respect to FIG. 3A. As discussed below, each array 36, 38 and 40 or other implanted device that is part of system 30 typically includes one or more components. Many of the components can have one or more operating state conditions that are adjustable. For each of these components, memory 75 stores data representative of the values of the operating states for these components. In FIG. 3B only the blocks 76, 77 and 78, for the operating state values for what is arbitrarily the nth component of the second array or device are specifically identified. For example, this component may be a current sink. The variable operating state values associated with this component may be, current level, pulse width, and pulse frequency. Each of the value fields may itself include plural sub-fields as seen in FIG. 3C. For example, the sub-fields for the current level value may include data indicating a minimum current level 76a; a present current level 76b; and a maximum current level 76c.

Processor memory 75 also includes a file 80 of component initial values. File 80 contains an indication for each device component an indication of the initial setting for that device. Thus, if a device is a current sink, the fields in file 80 for the device contain an indication of the initial magnitude of the level of current draw for the device, the time of the pulse width for which the device should be on and the frequency with which the device should be pulsed on. If the array component is a multiplexer used to connect current sources and sinks to the electrodes integral with a particular array 36 or 38, the initial values are data indicating to which electrodes the sources and sinks should be connected. If the array component is a sensor, the initial values may indicate the bandwidth of the signal that is to be sensed.

Another file stored in the IDC memory 75 contains target values for the sensed parameters. Each record in this file, file 81, contains data for a particular sensed parameter one of the device components is able to sense, the target values for the parameter.

Figures 4, 10:
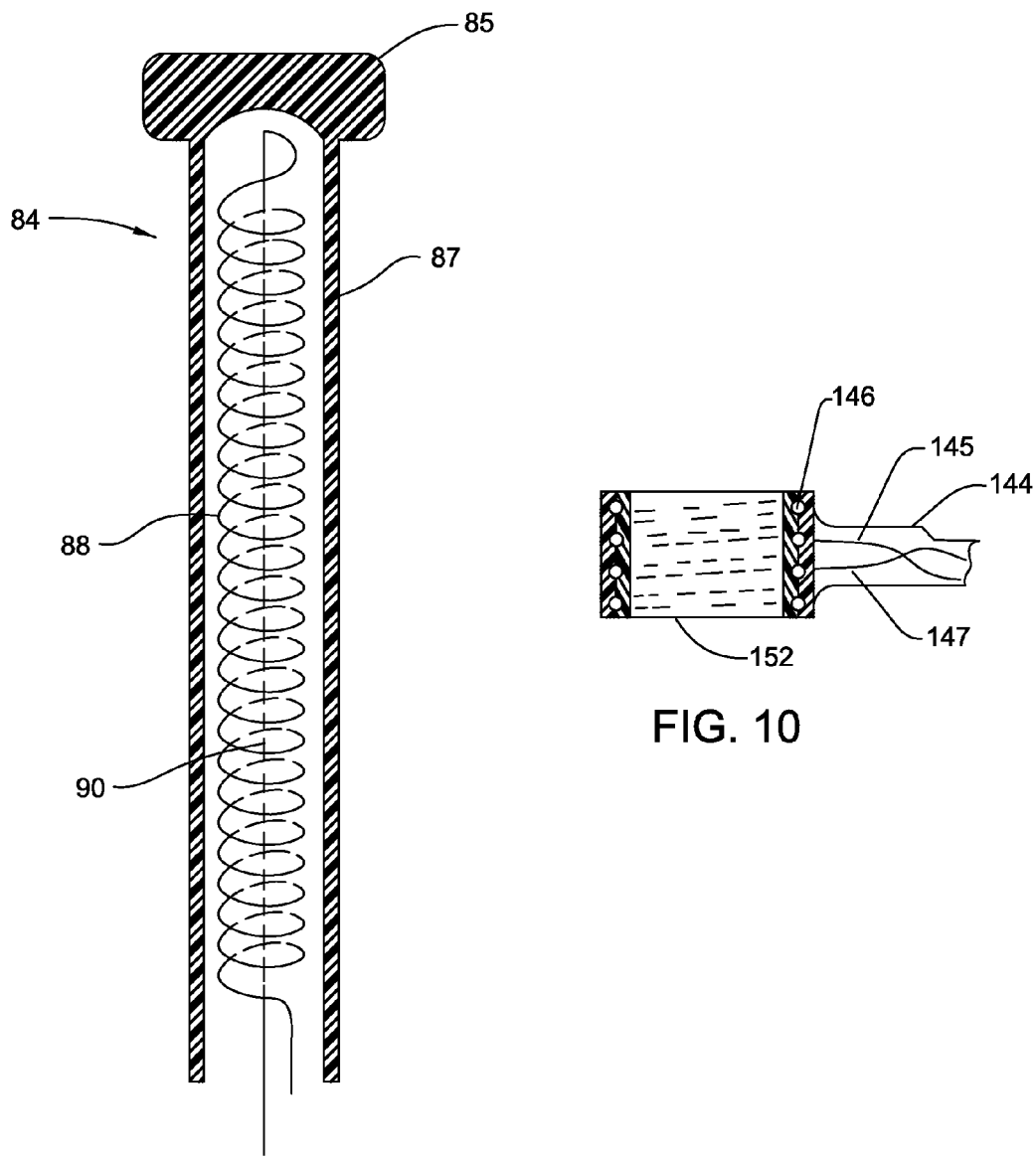
FIG. 4 is a partial cross sectional view and partial cut-away view of the bus trunk integral with the implantable device controller.
FIG. 10 is a cross sectional and partial top plan view of the branch bus and cuff.
Figure 5:
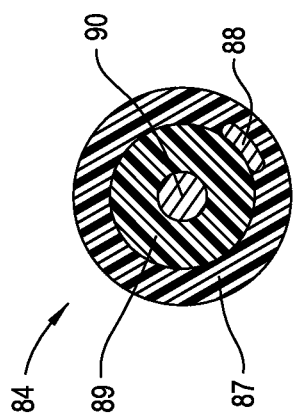
FIG. 5 is a cross sectional view of the bus trunk.

System bus 34 includes a bus trunk 84. Bus trunk 84 is the portion of the system bus 34 that physically extends directly from the IDC shell 42. The bus trunk 84, seen in FIGS. 3, 4 and 5, is a two-wire bus. One wire, wire 88, is in the form of a helix. A second wire, wire 90, extends through the center of the helix formed by wire 85. Wires 88 and 90 are connected at their ends distal from the IDC shell 42. The proximal end of wire 85 is connected to the LF modulator/demodulator 66 internal to the shell. The end of the wire 90 that extends back to the shell 42 is connected to the ground of the circuit internal to the IDC 32. For ease of illustration, in FIG. 3, the only other IDC components tied to ground are the rechargeable cell 58 and the HF signal generator 63. Wires 88 and 90 are formed from stainless steel and have a diameter no greater than 75 microns. Wires 88 and 90 are both coating in parylene (not illustrated) that insulates the wires. The parylene coating has a thickness of approximately 10 microns.

The return wire, wire 90, extends through the center of a core 89 formed from liquid crystal polymer or other flexible, biocompatible insulating material. Wire 88, the helically wound wire, extends around the outer surface of core 89. A shell 87, which may be formed from the same material from which core 89 is formed, extends over the exposed surfaces of core 80 and wire 82. In some versions of the invention, wires 88 and 90 are two sections of a single strand of wire. The section of the wire forming return wire 90 is molded in place when core 89 is formed. The section of the wire that extends out of the molded core 89 is wrapped first over the distal end of the core 80 and then wrapped around the outer cylindrical wall of the core to form helically wrapped wire 88. Shell 87 is then molded in place over the assembly consisting of coiled wire 88, core 89 and return wire 90.

Bus trunk 84 also includes, at its distal end, a cap 85. Cap 85 extends radially outward from shell 87 so as to have an outer diameter greater than that of shell 87. The cap 85 extends over the bent section of wire that forms the transition between wire 88 and wire 90. In some versions of the invention, when shell 87 is molded in place over wire 88, core 89 and return wire 90, cap 85 is simultaneously molded so as to be integral with the shell.

Figure 6:
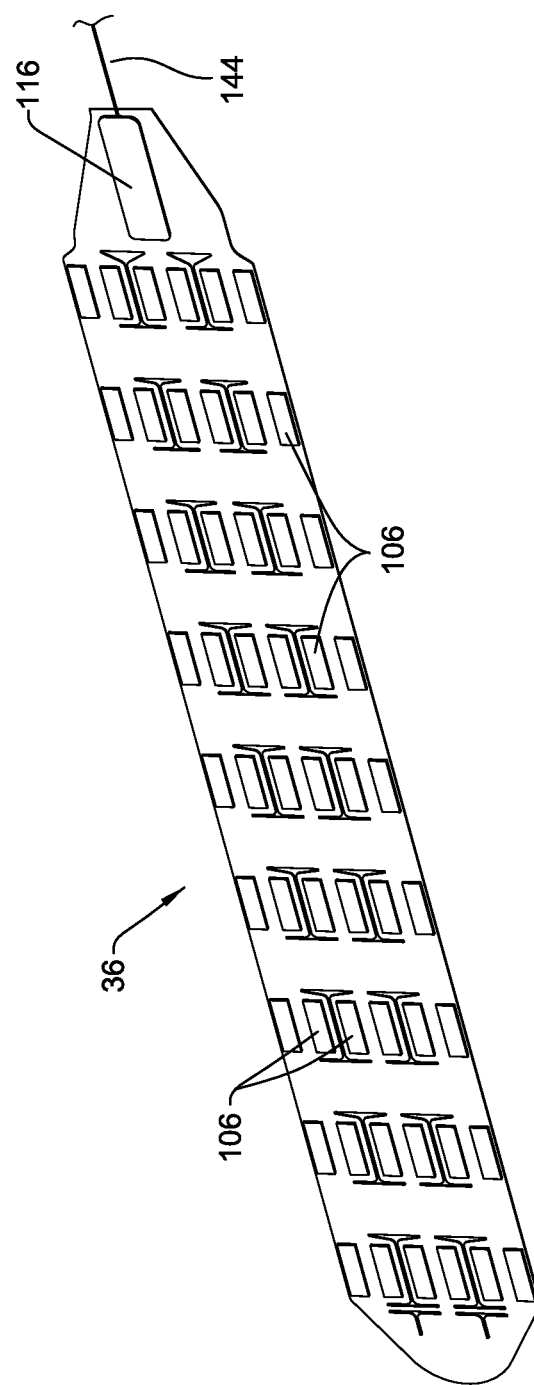
FIG. 6 is a perspective view of one electrode array that can be incorporated into the system of this invention.
Figure 7:
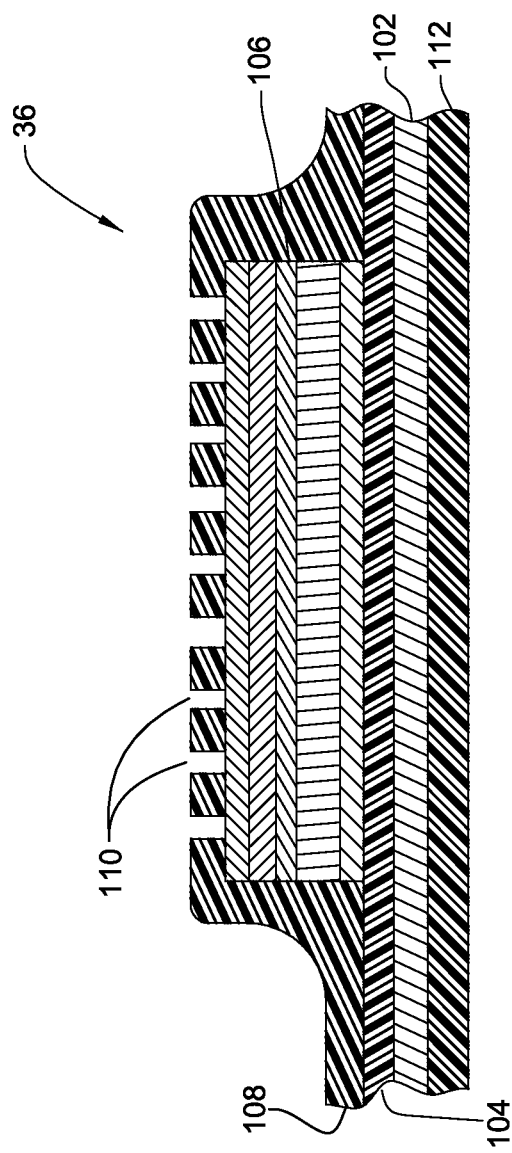
FIG. 7 is a cross sectional view of a single electrode of the electrode array of FIG. 6.

FIGS. 6 and 7 illustrate one type of electrode array, electrode array 36, which can be incorporated into multi-array system 30 of this invention. Array 36 is designed to be disposed against a section of tissue. For example, assembly 36 may be curved so as to be disposed over a section of the spinal cord dura. Array 36 includes a carrier 102 that forms the support structure for the other components of the array 36. In the illustrated version of the invention, carrier 102 is formed from metal. Accordingly the opposed faces and sides of the carrier 102 are coated with a biocompatible electrically insulating material.

A number of individual electrodes 106 are disposed on one side of the carrier 102. This side of the array is referred to as the "active" side of the array 38. A first layer of insulating material, layer 104 is disposed over the carrier 92 so as to be between the carrier and the electrodes 106 (one electrode seen in FIG. 6). In FIG. 7 the electrode 106 is shown as being formed from plural layers of electrically conductive material. The structure of the individual electrodes 106 or how the electrodes are disposed on the carrier 102 is not part of the current invention. A second layer of insulating material, layer 108, is disposed over both insulating layer 104 and the electrodes 106. Insulating layer 108 is provided with openings 110. Openings 110 are disposed over the electrodes 106. Openings 110 expose the outermost conductive layers of the electrodes 106 so that these layers are exposed to the tissue against which the array 36 is disposed. The current flow into and out of the tissue is through insulating layer openings 110.

In FIG. 6, the individual electrodes 106 appear as raised rectangles. This is for purposes of illustration. Slots not identified, are formed in the body of the electrode array 36. The purpose of these slots is disclosed in the Applicant's incorporated by reference PCT Pub. No. WO 2009/111142.

The side of array 36 opposite the side on which the electrodes 106 are disposed is referred to as the passive side of the array. In FIG. 7 insulating layer 112 is shown disposed over the face of the carrier 92 on the passive side of the array 36.

Figure 8:
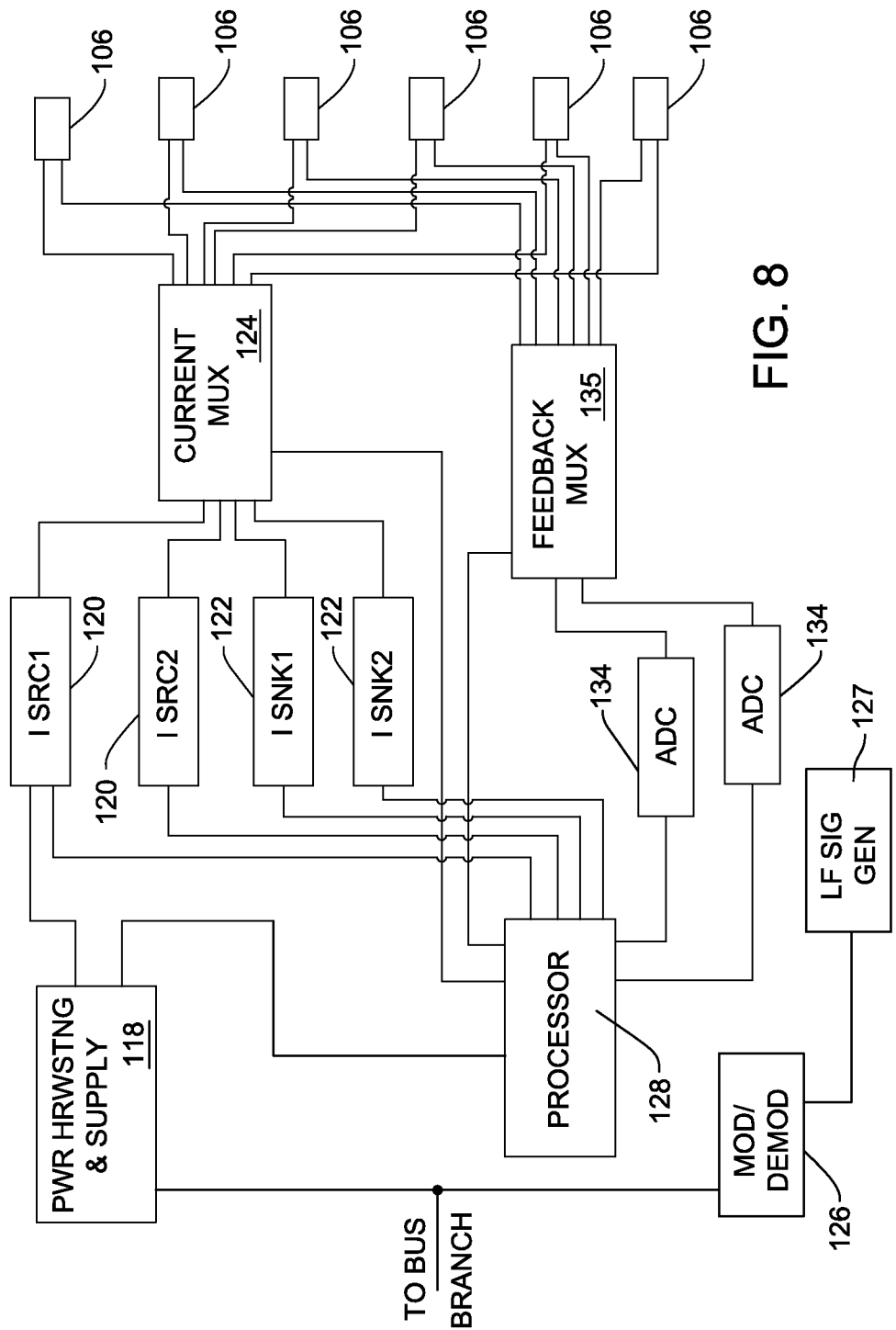
FIG. 8 is a block diagram of the sub-circuits internal to the drive module of the electrode array of FIG. 6.

A drive module 116 is mounted to carrier 102 on the active side of the array 36. Drive module 116 contains the components that source current from and cause the sinking of current into the individual array electrodes 106. As seen in FIG. 8, drive module 116 includes a power harvesting and storage supply circuit 118. Circuit 118 stores the charge in signals received from the IDC 32. The charge stored by circuit 118 powers the other components internal to drive module 116. For ease of illustration, only connections to one of the array current sources 120 and the control processor 128 are shown. Also not shown is (are) any voltage regulator(s) integral with the power harvesting and supply circuit. Also part of drive module 116 are plural current sources 120 (only two shown) and plural current sinks 122 (only two shown). Current sources 120 and current sinks 122, respectively, source current into and sink current out of the tissue adjacent the array 36 through the electrodes 106 (only six electrodes shown). Electrode array 36 is depicted as having more electrodes than there are combined current sources 120 and current sinks 122. A current multiplexer 124 connects each one of the current sources 120 and each one of the current sinks 122 to the electrodes 116. Current multiplexer 124 can connect any of the electrodes 106 to any one of the current sources 120 or current sinks 122.

In FIG. 8 conductors, not identified, are shown as extending between electrodes 106 and the current multiplexer 124. These conductors are traces of electrically conductive material that are disposed over the active side of the array. More particularly, the conductors are located between insulating layers 104 and 108 and extend to the electrodes 106.

The signals received by the array 36 from the IDC are also applied to a modulator/demodulator 126. Modulator/demodulator 126 extracts the control signals contained in the signals received from the IDC 32. The modulator/demodulator 126 is also capable of outputting modulated signals that contain data regarding the array 36 to the IDC 32. Specifically, modulator/demodulator 126 modulates the signals produced by a signal generator 127 also part of the drive module 116.

Drive module 116 also includes a control processor 128. Processor 128 regulates the magnitude of the current sourced and sunk by, respectively, each source 120 and sink 122. The processor 128 also asserts control signals to current multiplexer 124. Based on the signals asserted by processor 128, multiplexer 124 connects each source 120 and sink 122 to the appropriate electrode/electrodes 106.

Figure 8A:
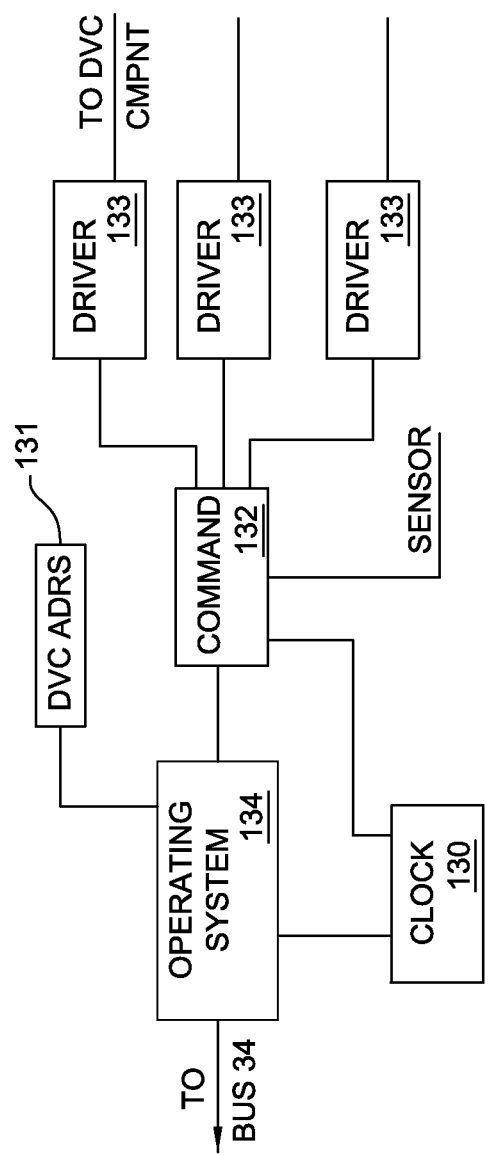
FIG. 8A is a block diagram of modules that run on the processor internal to the array drive module.

A number of different software modules, now described by reference to FIG. 8A are run on control processor 128. One of these modules is an operating system 129. Operating system 129 controls the overall operation of the processor 128. The operating system 129 also is responsible for processing the incoming data and instructions received over bus 34. Operating system 129 also controls the outputting of data by processor 128 for transmission over bus 34. Stored within operating system 129 is a device address, represented by block 131. The device address identifies with specificity the particular array 36, 38 or 40 or other device connected to bus 34.

A clock 130 also runs on the processor 130. Clock 130 keeps a time that is identical to the system time maintained by the IDC clock 69.

Figure 11:
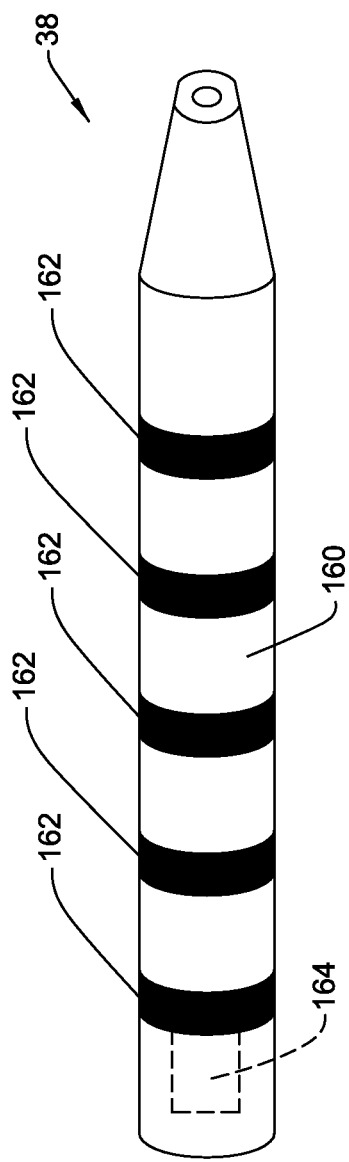
FIG. 11 is a perspective view of a second electrode array that can be component of the system of this invention.

A command module 132 asserts the instruction signals that regulate the other components that form the array or device with which the processor 128 is integral. The command module 132 receives device commands 184 (FIG. 11) transmitted from the IDC 32. The command module processes each command and outputs the command as an instruction signal.

In many versions of the invention, the instruction signals output by the command module are applied to drivers 133 (only three shown) also run on the control processor. A driver 133 converts the instruction signals into a device-specific drive signal. For example, each current source and current sink may have its own driver 133. The driver 133, in response to a source/sink specific instruction signal that is digital form, may output an analog-state drive signal to regulate the level of the current to be sourced/sunk by the receiving component. Depending on the type of component, the driver 133 may also simply convert the digital instruction signal into a serial bit stream.

Drive module 116 is also capable of generating output signals regarding the state of the array or other device with which the module is integral and data regarding parameters measured by the array or device. In FIG. 8, the ability of the electrode array to measure parameters relevant to the operation of the system is represented by the presence of two analog to digital voltage converters (ADCs) 134. Each ADC 134 can be connected to one of the array electrodes 116 to measure the voltage present at the electrode. In the illustrated version of the invention there are more electrodes 106 than ADCs 134. The ADCs 134 are connected to the electrodes 106 over a feedback multiplexer 135, also part of drive module 116. In the illustrated version of the invention, feedback multiplexer 135 simultaneously connects any of the two electrodes 106 to separate ones of the two ADCs 134.

In FIG. 8A, the relationship between the ADCs 134 and the processor 128 is represented by the line marked SENSOR that extend to the command module 132. This reflects that the data the drive module 116 may transmit over bus 34 may be more than simply voltage measurements. Other devices that are part of the system 30 of this invention may include transducers capable of generating sensor signals representative of physiological parameters such as ionic currents or pH levels.

The command module 132 is further capable of generating instruction signals used to regulate the operation of the array or device sensing circuits. These instructions may regulate such things as, the amplification of the signals produced by the actual transducer element. Alternatively, these instructions may include coefficients used to regulate the filtering and/or band pass of the sensor signals by the filter unit to which the transducers are connected. These instructions may be forwarded to transducer specific drivers 133. The drivers convert the signals into device-specific drive signals. Alternatively, these instructions may be forwarded directly to the transducer assemblies for which the signals are intended.

Figure 9:
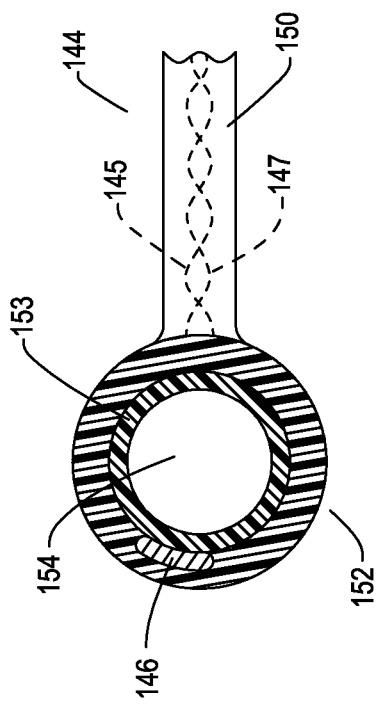
FIG. 9 is a cross sectional view, of the cuff integral with a branch bus that view being taken in a plane in which the longitudinal axis of the bus lies.

A bus branch 144, now described by reference to FIGS. 9 and 10, extends between electrode array 36 and bus trunk 84. The bus branch 144 includes two wires 145 and 147 that extend from the array drive module 108. Wires 145 and 147 may be formed from the same material and have the same characteristics as bus trunk wires 88 and 90. Wires 145 and 147 are connected together at their distal ends by a coil 146. In some versions of the invention, wire 145, coil 146 and wire 147 are different sections of the same strand of wire. Also, while not illustrated, wire, 145, coil 146 and, wire 147 may, like bus trunk wires 88 and 90 be covered with an electrically insulating coating.

Wires 145 and 147 are encapsulated in a sleeve 150 formed from liquid crystal polymer or other electrically insulating, flexible biocompatible material. Coil 146 is contained in a tube-shaped cuff 152. In one version of the invention, bus branch 144 is formed by first molding a tube like inner shell 153. Inner shell 153 has a through bore 154 with a diameter that is typically 50 microns or more larger in size than the outer diameter of bus trunk shell 87. A portion of a wire strand is wrapped around the outer cylindrical surface of the inner shell 153 to form coil 146. The wire is wrapped so that the sections of the wire that extend from coil 146 are of sufficient length to form wires 145 and 147. Liquid-state liquid crystal polymer is applied over the wires 145 and 147, the exposed surfaces of coil 138 and the exposed face of the inner shell 146. Upon curing, this liquid crystal polymer forms both an outer shell 155 of cuff 152 and the flexible sleeve 150 around wires 145 and 147.

In some versions of the invention, prior to the formation of case 150, wires 145 and 147 are twisted together. This provides strength to the bus branch 134. Also, the material forming sleeve 150 may be formed to extend to a partially cover drive module 116.

Electrode array 38 is what is commonly referred to as a ring electrode array. Electrode array 38 consists of a cannula 160. A number of electrodes 162 are disposed around the outer surface of the cannula 160. Some versions of array 38 are constructed so that the electrodes 162 extend completely circumferentially around cannula 160. Other versions of array 38 are constructed so that one or more the electrodes 162 extend only partially circumferentially around the cannula 160. An electrode array 38 for integration into system 30 of this invention may even be constructed so that in one lateral slice section through the array 38, one electrode extends around one arcuate segment of the cannula and a second electrode, that is arcuately spaced away from the first electrode, extends around a different arcuate segment.

Electrode array 38 has a drive module 164 (shown in phantom). Drive module 164 may be similar to previously described drive module 116. That is, internal to the drive module are components for sourcing current from/sinking current to the individual electrodes 162. If the number of current sources/sinks is equal to the number of electrodes, drive module 164 may not require the multiplexer located between the current sources/sinks and the electrodes 162. Depending on the particular construction of the drive module 164 it may or may not include the ADC circuits for generating digitized representations of the voltages present at the electrodes 162. If the ADC circuits are not present, the need to provide a multiplexer for these circuits is likewise not present.

Figure 12:
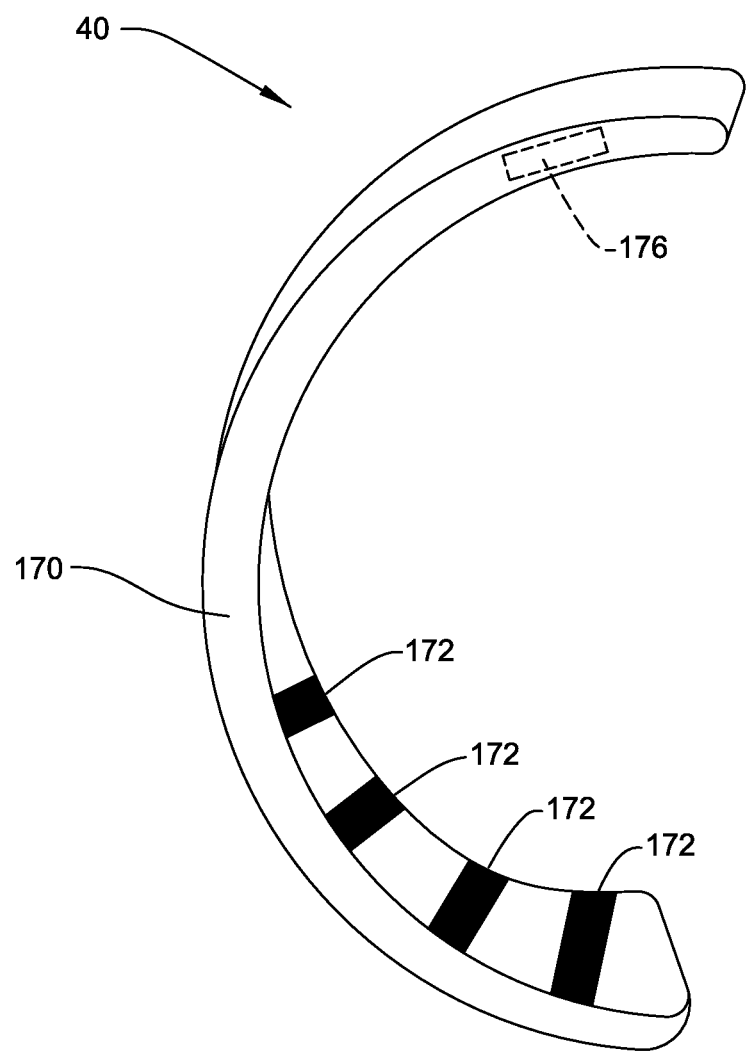
FIG. 12 is a perspective view of a third electrode array that can be a component of the system of this invention.

System 30 of this invention is shown as having a third electrode array, array 40, seen best in FIG. 12. Array 40 is what is known as a cuff electrode. Electrode array 40 includes a substrate 170 formed of silicone. Substrate 170 is formed so the substrate can be wrapped around a section of tissue such as a nerve bundle. A number of electrodes 172 are formed on the substrate 172 at locations that are longitudinally spaced apart from each other along the length of the substrate.

In one version of the invention, electrode array 40 is not intended to flow current through the tissue against which the array is disposed. Instead, electrode array 40 is designed to provide signals back to the IDC 32 indicating the strengths of the voltages measured by the electrodes 172. Accordingly, also disposed on substrate 170 is a transponder 176. Transponder 176 has many of the components of the drive module 116 of FIG. 8. There is a power harvesting and storage circuit; a low frequency generator; a modulator/demodulator; and a processor. There are also one or more ADCs, similar to ADCs 134, capable of generating digitized versions of the signals present at the electrodes 172. If there are more electrodes than ADCs a feedback multiplexer, analogues to multiplexer 124, selectively connects the electrodes 172 to the ADC.

In FIGS. 1 and 2 the only devices shown connected to the IDC 32 over bus 34 are the arrays 36, 38 and 40. Other devices that are not array like (with multiple electrodes or multiple transducers), may be part of system 30. Often these additional devices are other types of sensors that have a single sensing transducer. One such device is a pressure transducer that monitors the blood pressure in a vessel of the individual in whom system 30 is implanted. Accordingly in this document the system is described as having arrays or other devices that are connected to the ID 32 over the common bus 34. Unless otherwise specifically stated, descriptions of the exchanges of signals between the IDC and the arrays and the response of the arrays to IDC-output commands should be understood to be the arrays or other devices connected to the bus 34.

Figure 13:
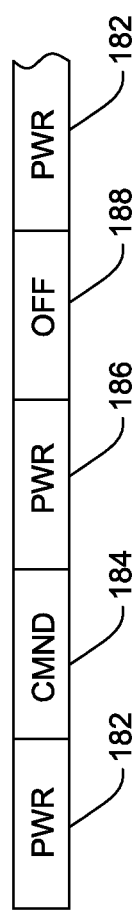
FIG. 13 depicts a sequence of signals that are transmitted over the system bus by the implantable device controller.

FIG. 13 illustrates one sequence in which the IDC transmits signals. As represented by time blocks 182, when the IDC is not transmitting commands to the arrays 36, 38 and 40, the IDC outputs power signals from the LF signal generator 65 over bus 34 to the electrode arrays 36, 38, and 40 or any other devices connected to the bus. Block 184 represents the transmission of a command by the IDC processor 62 to one of the electrode arrays 36, 38 or 40 or other devices. The command 184 is transmitted by having the LF modulator/modulator 66 module the signal output by the LF signal generator 65. In FIG. 13, the transmission of this command is followed by the transmission of additional block 186 of unmodulated power signals. There are time periods in which the IDC does not output signals over bus 34; the signal from generator 65 is not output over bus trunk 74. Off block 188 represents one of these blocks. These time blocks in which the IDC does not transmit signals over bus 34 are to provide periods in which the electrode arrays 36, 38 and 40 or other devices connected to bus 34 can transmit information back to the IDC 32. The partial depiction of a power block 182 on the right side of FIG. 13 represents the repeat of a new cycle of the IDC transmitting power and commands to and waiting for responses from the electrode arrays 36, 38 and 40.

Figure 14:
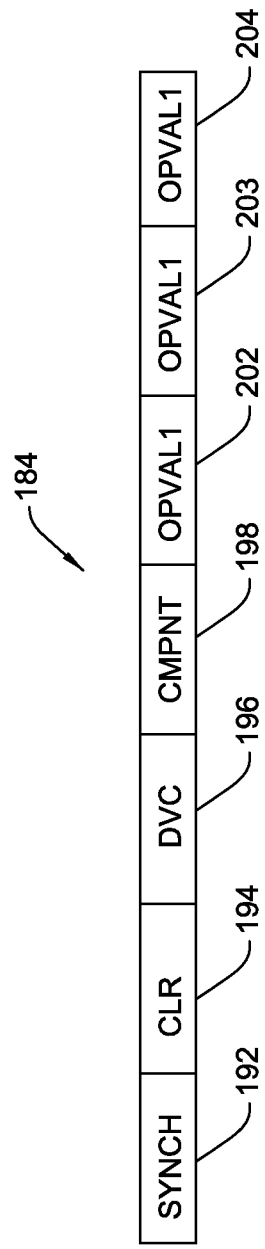
FIG. 14 depicts the sequence of signals that comprise an IDC generated command that is transmitted over the system bus to the electrode arrays and other devices connected to the FIGS. 15A and 15B collectively form a flow chart of the processes executed by one of the electrode arrays of the system of this invention.

FIG. 14 represents, in more detail, the format of a command, the material in block 184, that the IDC transmits to the electrode arrays 36, 38 and 40 or other devices. Block 192 of the command represents the transmission of a set of synchronization signals. The synchronization signals serve to place the array modulator/demodulators in a state in which they are able to demodulate the subsequent portions of the received command. A clock (CLK) signal 194 follows the synchronization signals of block 192. The clock signal, based on the clock time from the IDC clock 69, includes data applied to the individual clocks 130 internal to the array/device drive modules/transponders to reset their clock times. A device (DVC) block 196 contains an address that indicates the array or device to which the IDC-generated command is intended.

The device block 196 is followed by an component identification (CMPNT) block 198 followed in many instances by one or more opvalue blocks (OPVALx), blocks 202, 203 and 204 in FIG. 14. The component identification block 198 contains an address specific to the on array (or device) component for which the command block 184 is intended. Thus, component block 198 may indicate that the command is intended for one of the current sources 120, one of the current sinks 122, the current multiplexer 124 or one of the ADCs 134. The opvalue blocks 202-204 contain data that define the command. These data can indicate whether or not the component should be turned on or off. Opvalue block data also include values associated with command. For example if the device is a current source or sink the opvalue may contain information indicating the level of the current the device should source/sink. An additional type of data contained in the opvalue block 202, 203 or 204 is an indication of to which electrode 106 the particular source (or sink) should be connected. A third type of data contained in an opvalue block 202, 203 or 204 is an indication of when the array or other device should execute the steps required to perform the command.

The signal output by the IDC 32 on bus trunk 74 is an alternating current signal. Accordingly, as a consequence of the close proximity of the cuffs 152 integral with the bus branches 144, the signal is transferred by inductive coupling to the cuffs 152 integral with the bus branches 144. From each bus branch 144, the signal is applied to the drive module/transponder 126 to which the branch is connected.

The process steps performed by an electrode array 36, 38 or 40 are now described by reference to FIGS. 15A and 15B. Step 212 illustrates the processing of the power signals by the array power harvesting and supply circuit 118. Specifically, circuit 118 rectifies the signals received over the associated bus branch. The power contained in the rectified signal is stored by circuit 118. The stored power is applied to the other circuits internal to the drive module/transponder to power these circuits.

Figure 15A:
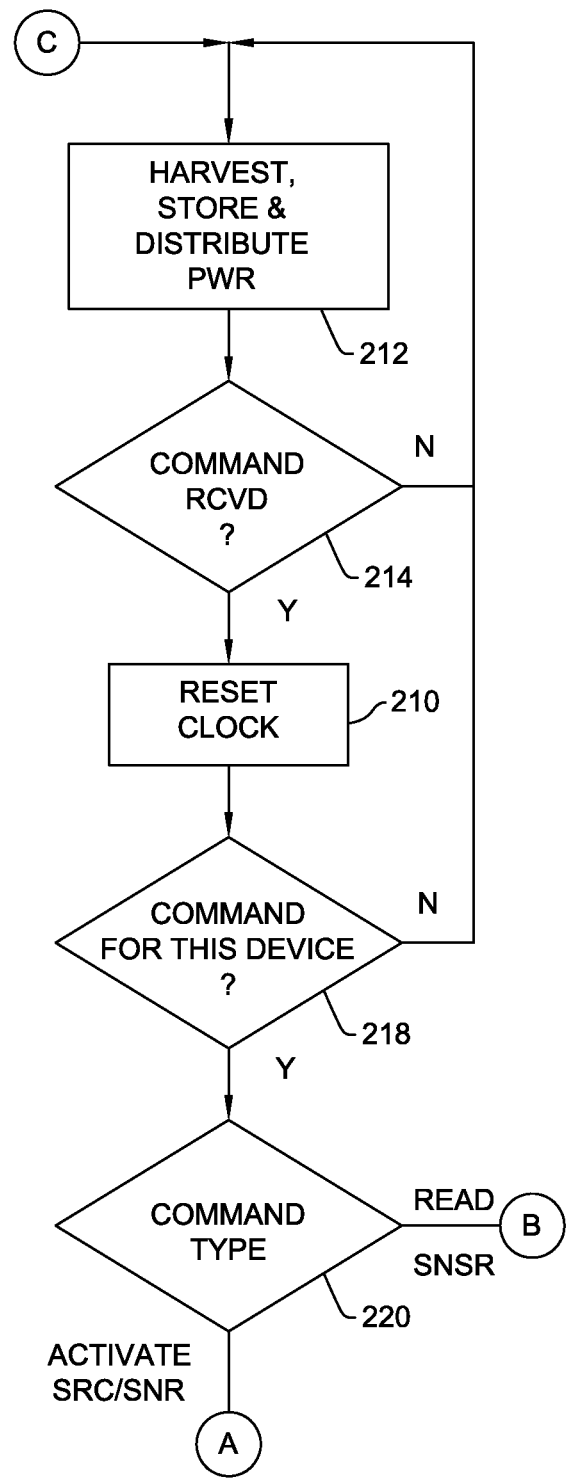
Figure 15B:
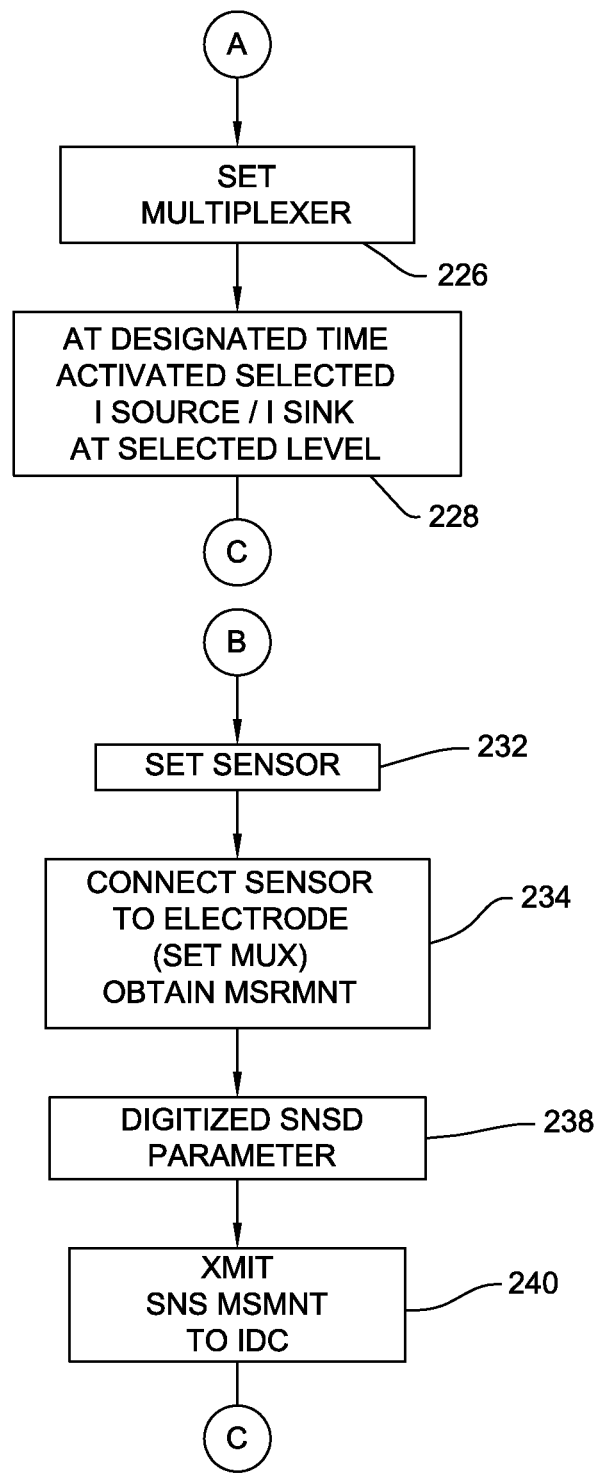

In FIG. 15A, step 212 is shown as only occurring until a command block 184 is received. This is for simplicity of illustration only. Power harvesting and storage circuit 118 rectifies and stores more than the power contained in the signals within the power signal blocks 182 and 186. Circuit 118 also rectifies, stores and distributes the power contained within the command block 184 signals output by the IDC 34.

The power signals received by each electrode array are also applied to the modulator/demodulator 126 integral with the array. Since these signals are not modulated, they are not processed by the modulator/demodulator 126.

The IDC processor 62 transmits a command block 184 by having the IDC modulator/demodulator 66 modulate the signal output by the LF signal generator 65. The signal is modulated based on the contents of the command generated by processor 62 and applied to modulator/demodulator 66. Initially, the LF signal is modulated to produce the synchronization signal. The modulated signal broadcast over bus 34 is demodulated by the drive module/transponder modulators/demodulators 126. Signals comprising the demodulated signals are forwarded to the processors 128 internal to the drive module/transponders. In a step 214 the operating system modules 129 run on the processors 126 use the receipt of the initial block of signals that form a command block, the synchronization block 192 signals, as an indication that a command is being received. The loop comprising steps 212 and 214 is meant to represent that, processors 126 continually monitors the received signals to determine if a command block 184 has been received.

Upon receipt of an IDC-generated command, the processor operating systems 129, in a step 216, uses the data in clock signal section 194 to reset the drive module/transponder clock 130. This is to ensure the devices that form system 30 execute time-sensitive instructions based on a time that is essentially identical across the system.

The drive module/transponder processors 128 then review the command block device code. The data in this block are read to determine if the code indicates if the command is for the electrode array 36, 38 and 40 with which the processor is integral, step 218. More particularly, the processor operating systems 129 determine if the device address in block 196 is identical to the stored address 131. If the command is not for that particular electrode array or device, the command is ignored. This is represented in FIG. 15A by the loop back from step 218 to step 212.

The processor 128 integral with the electrode array or other system device for which the received command 184 is designated then proceeds to execute step 220 to determine the type of command. Essentially the IDC generates one of two types of commands: (1) a command to activate/deactivate a current source/sink; or (2) a command to receive data from one of the sensing components integral with the array or device. The array processor 128, in step 220 determines the type of command it has received based on the data in the command opcode block 198. This determination is typically made by the processor command module 132. The processor 128, more particularly the command module 132 determines for which component the command is intended based on the data in the component block 198. The values associated with the command are based on the data in the one or more opvalue blocks 202-204.

If the command is an instruction to cause current to source/sink current through one of the electrodes 106 or 162, the processor command module, in a step 226, initially has the current multiplexer 124 establish a connection between the current source/sink that is to source/sink the current and the specific electrode 106 or 162 through which the current is be flowed. This step 226 is executed by having the processor command module 132 generate the appropriate instruction for the multiplexer 124. Given that the multiplexer most likely responds to digital signals, this instruction may be applied directly to the multiplexer and not be applied through a driver 133.

Once the source/sink to electrode 106 or 162 connection is established, in a step 228 the processor 128 sets the designated source 120/sink 122 to source/sink the designated current. Specifically, based on the received command 184 and the opvalues contained in the command, the processor command module generates an instruction that the designated source/sink should source/sink current. The instruction, based on the current level indicated in the received command 184, designates the level at which the current is to be sourced/sunk. Further, it should be understood that command module generates this instruction so the current is sourced/sunk at the time designed in the received command 184. Thus, after adjusting for propagation delays, the instruction may generated at the when the time as indicated by the device clock 130 is equal to the designated execution time as specified in the command.

In step 228 command module 132 forwards the generated instruction to the driver 133 connected to the device component for which the instruction is intended. The driver 133 converts the signals comprising the instruction into a form in which the component can respond to the instruction. The conclusion of step 228 can be considered the receipt of the instruction by the component.

While technically not a command to "activate" a current source or sink, the command may be one in which the drive module 116 is instructed to stop sourcing (or sinking current through a particular electrode 106 or 162. In this situation the command block opvalues include data that: instruct the active source (or sink) to stop sourcing (or sinking current; and disconnect the source (or sink) from the electrode 106 or 162. Likewise an "activate" command may be a command to adjust one of the characteristics of the current being source (or sunk) through an electrode. In this situation, the particular source 120 (or sink 122) is already connected to the electrode. It may therefore not be necessary to generate an opvalue and execute step 226 to establish the source (or sink) to electrode 106 or 162 connection.

In step 220, the command module 132 may determine that the IDC-generated command 184 is one in which the IDC processor has requested sensor or component status information. In this situation, the command module 132 configures the components necessary to generate the desired information. As represented by step 232 of FIG. 15B, this may involve asserting instructions to the on-device components that generate the desired information. Given that the sensing component may be something other than an ADC, step 232 is called out as the SET SENSOR step. For example, this may involves setting some of the signal processing components, the ADC 134 that will output the digitized representation of the voltage to be measured. These instructions may be forwarded directly to the component. Alternatively, the instructions may be forward to the driver 133 associated with the component. The driver 133 converts the instructions into a form in which they can be acted upon by the component for which. The responding of the component to the configuration instructions can be considered the conclusion of step 232.

Once the parameter sensing component is properly configured, it may be necessary to execute a step 234. In step 234 the component is connected to the electrode 106 or 162 employed to perform the sensing operation. Here, the command module 132 generates the appropriate instruction to cause the feedback multiplexer 135 to connect the sensing circuit to the designated electrode 106 or 162. It should be appreciated that the command module 132 may cause this connection to occur at a time based on a time based on the IDC generated command 184. Again, if this is a time based command, the instruction is generated by reference to the time specified by clock 130. Integral with step 234 is the actual obtaining of the measurement of the sensed parameter.

Step 236 represents the digitization of the parameter monitored by the sensing component. This step 236 may be performed by the component itself or software that is part of the command module 132.

Once the signal representative of the sensed parameter is digitized, in a step 238, the parameter is transmitted to the IDC processor, step 240. In step 240 the digitized sensed parameter is forwarded from either the sensing component or the command module 132 to the operating system module 129. The operating system module 129 outputs the data representative of the command over the bus 34. More particularly, in this process, the operating system module 129 initially activates the LF signal generator 127 integral with array/component. The operating system module 129 forwards the data containing the sensed parameter to the modulator/demodulator 126. The modulator demodulator then outputs a modulated signal co containing the command over the bus 34 and more particularly the bus branch 144. Inductive coupling causes the signal to be applied from the cuff 152 to the adjacent bus trunk 86. The signal travels from the bus trunk to the modulator/demodulator 66 internal to the IDC 32. The LF modulator/demodulator 66 extracts the sensor data signals from the signal stream applied to the bus trunk 66. The extracted signals are forwarded to the IDC processor 62. The IDC processor, as discussed below, further regulates operating of system 30 based on these signals.

While not illustrated, the format in which arrays 36-40 and other devices write data back to the IDC is similar to the format of the signals comprising a command block 184. The set of signals includes a block of synchronization signals. The IDC modulator/demodulator 66 uses the synchronization signals to facilitate the demodulation of the following signals. The next block of signals may include data identifying the device transmitting the data. The next block of signals is the actual data.

It should be appreciated that an array 36, 38 or 40 or other device connected to bus 34 should only transmit signals over the bus at times at which the IDC 32 is not outputting signals. Accordingly, as part of the process of the execution of step 240, the operating system asserts the signals that causes the outer components of the array or device to output data over bus 34 during one of the designated off blocks 188 in which neither the IDC nor any of the other system devices is transmitting signals over the bus. To ensure transmissions back to the IDC occur in this time period, the IDC 32, when it generates a command requesting information back from a device component, includes an opvalue 202, 203 or 204 indicating when the information should be transmitted. The operating system module 129, by reference to the device clock 130, as part of step 240, asserts the signals that cause the transmissions over the bus 34 at the time designated by the opvalue.

Once the data are transmitted over bus 34, step 240 concludes with the deactivation of the device low frequency signal generator 127. This sub-step is performed to minimize the power draw of the components forming the array 36, 38 or 40 or other device.

As represented by the loop backs from steps 228 and 240 to step 212, the array/device drive module/transducer continually harvests power while waiting for commands the device/array is to execute. Also, a number of the steps executed by the array/device may be executed concurrently. For example, once a command is received to source current from/sink current into a particular electrode, the array may activating the appropriate current source/sink and establishing the necessary electrode connection, hold the source/sink active while maintaining the electrode connection. The array maintains this operating state until it receives a further command 184 instructing it to adjust this operating state or deactivate the source/sink.

System 30 of this invention is readied for use by initially determining through what tissue the patient would benefit if current is flowed therethrough. This process may involve positioning one or more trial electrode arrays in the patient. Current is flowed through the electrodes of these arrays to determine if such current flow provides the beneficial effects with, ideally, tolerable side effects. Other trial electrode arrays or other sensing devices may be implanted into the patient. These arrays monitor the signals transmitted by the patient's nervous system. The other sensors monitor other parameters of the patient's physiology. If the system 30 is to be implanted to provide relief from the perception of pain, an array of sensing electrodes is used to identify the nerves through which the pain signals are transmitted. The data obtained from the placement of the trial electrode arrays and other devices are used to determine where the arrays 36, 38 and 40 and other devices that are part of the system are to be implanted.

Figure 16A:
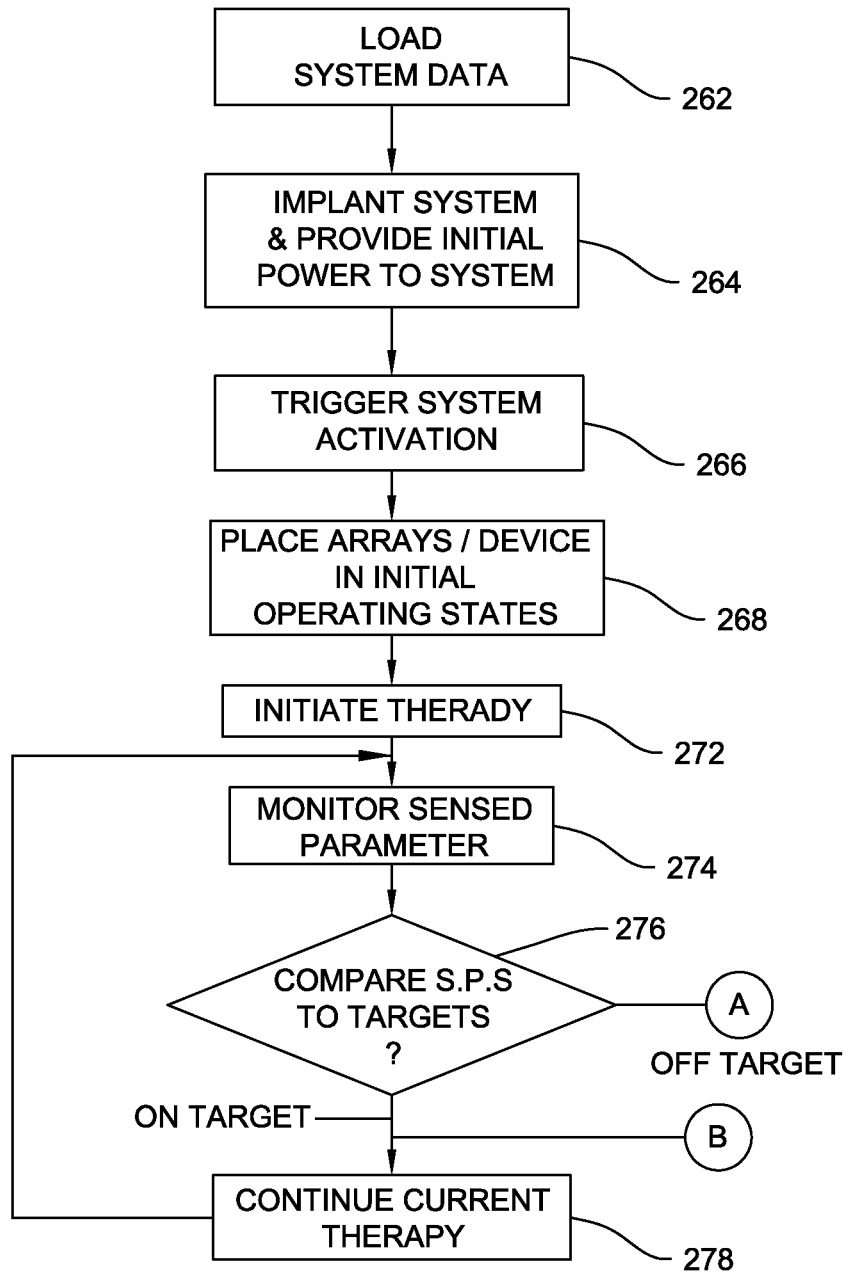
FIGS. 16A and 16B collectively form a flow chart of the processes executed during the operation of the system.

As part of this process, the IDC memory 75 is loaded with data forming blocks 76, 77 and 78 that describe the characteristics of the array and device components, step 262 of FIG. 16A.

Also as part of this process, a preliminary determination is made of through which electrodes the current should be flowed and the magnitude of the current flows. As part of step 262, these data are loaded in component initial value file 80 also in IDC memory 75. Also loaded into memory 75 are the address data that identifies the device components.

Another step in the process of preparing the system for operation is the determination of the target values for the parameters monitored by the device sensing components. These data may be generated based on variables such as empirical data or data generated during the pre-implantation evaluation of the patient. In step 262, these data are loaded into the target values file 81 internal to the IDC memory 75.

Also loaded into memory 75 as part of step 262 is the device update module 71. During step 252 one or more of the other software modules run on the IDC processor 62 may also be loaded in the IDC memory 75.

Prior to implantation, the components forming at least part of the system 30 are assembled together. (Step not illustrated) The bus branches 144 are coupled to the bus trunk 86 by fitting the cuffs 152 over the trunk shell 87. The cuffs 152 are fitted over the end of the trunk opposite the end to which cap 85 is mounted. The bus branches 144 are coupled to the bus trunk in the order opposite that of their proximity to the IDC 32. Bus trunk 86 is then connected to the IDC 32. System 30 of this invention is now ready for implantation, step 264. The method of implantation and electrode array deployment is not part of this invention.

Also as part of step 264, power is supplied to the IDC 32. This power is stored in cell 58.

Once the system is implanted and cell 58 charged, an external control device, not illustrated, is used to, in step 266, trigger activation of the system 30.

In response to receipt of the trigger instruction, the IDC processor 62 in a step 268, places arrays 36, 38 and 40 in their initial operating states. Specifically, the processor executes the device initialization module 70. The instructions in the device initialization module 70 cause the processor to send instructions to the individual arrays/devices that cause the array/device processors 128 to generate instructions to place the array/device component in the pre-defined initial operating states. These initial operating states are the states specified in the component initial data file 80.

In step 272, and in the other steps in which the IDC processor 62 generates commands 184 to the other devices that are part of the system, the commands include device and component addresses as indicated in the preloaded data: the data in the component initialization file 80; or data based on the instructions generated by the device update module 71.

Upon receipt of the command blocks 184, the arrays configure their components for operation based on the instructions based in the commands. In the described versions of the invention, selected ones of the current sources and current sinks integral with arrays 36 and 38 are configured to source/sink current. This is to cause the current to flow through the specific tissue where it is believed that such current flow will be an effect therapy. Specific ones of the ADCs of arrays 36, 38 and 40 may be connected to specific electrodes 106, 162 and 172, respectively. These connections are made to monitor voltage signals that indicate whether or not present current flow is offering effective therapy. In FIG. 14A, this initial activation of the system devices is represented as initiate therapy step 272.

Once therapy is initiated, the IDC processor 62 monitors the patient to evaluate whether or not the therapy is affective and/or whether or not the side effects are tolerable. Step 274 represents the actual monitoring, receipt of the signal representing the parameter sensed by the electrode arrays or other devices. The data representing these parameters are transmitted over bus 34 in the off blocks 188 in which the IDC 32 is transmitting neither power not instructions. These data are read out from the arrays or other devices based on the instructions contained in the parameter sense module 72. Based on instructions contained in the parameter sense module 72, as part of step 274, the IDC processor 62 prepares the data for it can be analyzed in the following step, compare step 276.

In the compare step 276, the IDC processor 62 analyzes the received data based on instructions contained in the parameter compare module 73. This analysis may be the comparison of waveform generated during the parameter sensed step 282 to a target waveform retrieved from target values file 81. Alternatively, a comparison of step 276 may be the less complex comparison of a voltage level generated in step 274 to a target voltage step.

Also in step 276, the IDC processor 62 determines whether or not the current therapy is effective and/or not responsible for side effects that may not be tolerable. Step 276 is shown as a single decision block. This is for ease of illustration. In practice, this determination may be made on the IDC processor: determining the extent to which a number of different sensed parameters are at their target levels; and performing a weighted analysis to determine if the on/off target evaluations of the sensed parameters collectively indicate that the current therapy is effective.

If the current therapy is effective, the IDC processor 62, as represented by step 278, maintains the current therapy regimen. Processor 62 does not change the instructions that result in current at specific levels being source and sunk through specific electrodes 106 or 162. The IDC processor 62 repeatedly reexecutes steps 274 and 276 to continue to evaluate the effectiveness of the therapy. This constant reevaluation is performed because changes in the patient's activity may indicate that a different therapy regimen needs to be applied to the patient. These changes may be due to the patient changing from a sleep state to an awake state. Alternatively, the changes may due to the patient transitioning from a sitting state to a walking state and then back to a sitting state.

As a result of the evaluations of steps 274 and 276 it may be determined that the effectiveness of the therapy is below the target level and/or the side effects may not be tolerable. In this event, the IDC processor 62 proceeds to execute the device update module 71. Based on the instructions in the device update module 71, the IDC processor 62 generates commands 184. These commands cause one or more of the arrays 36 or 38 to reset the current flow through the tissue adjacent the array, step 282 of FIG. 16B. The sequence by which the current flow is reset is a function of the number of parameters that can be reset on the on array devices that source/sinks current. An example of one protocol that may be followed for a current sink is:

1) Increase amplitude of sunk current
   If Not Successful
2) Decrease amplitude of sunk current
   If Not Successful
3) Increase pulse duty cycle of sunk current
   If Not Successful
4) Decrease pulse duty cycle of sunk current
   If Not Successful
5) Increase pulse repetition frequency of sunk current
   If Not Successful
6) Decrease pulse repetition frequency of sunk current
   If Not Successful
7) Terminate the sinking of current through the target electrode and start sinking current through an adjacent electrode.

Figure 16B:
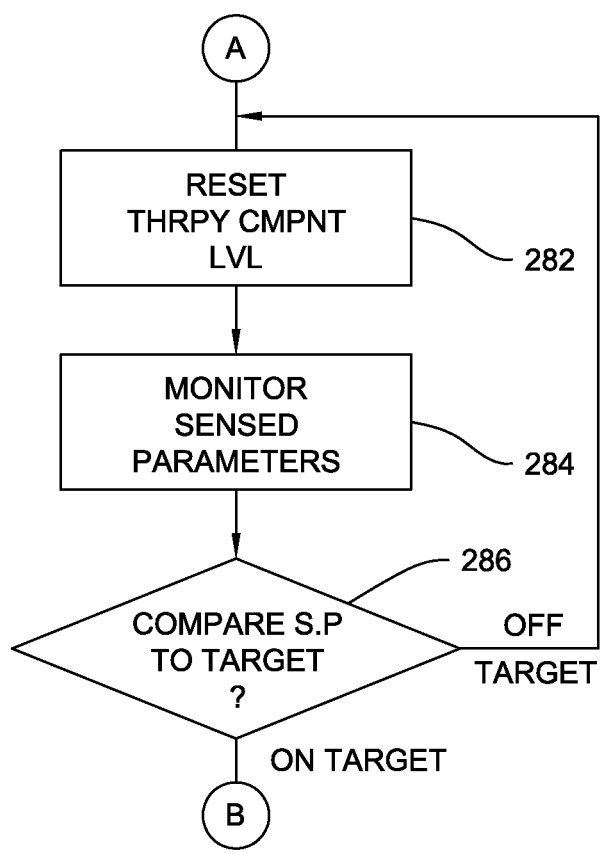

Each one of the above adjustments is performed by first performing a single step adjustment of the characteristic being adjusted. After this adjustment, the IDC processor 62 monitors the sensed parameters to determine if the adjustment has resulted in the system 30 providing therapy closer to the target result. In FIG. 16B, the monitoring of the sensed parameters is represented as step 284. Step 284 is analogues to step 274.

The comparing of the sensed parameters is represented as step 286. Step 286 is similar to step 276. If, as a result of the comparison of step 286, it appears that the sensed parameter is closer to the target values, the device update module 71 may include instructions that cause the IDC processor 62 to continue to make the particular step adjustment. More specifically, the step adjustment is made until the sensed parameter is within the range specified by the target values. For example, the device update module can be in a loop in which it causes the IDC processor 62 to generate commands 62 that cause one of the current sources 120 to increase the duty cycle at which it sources current. The comparison of step 286 may indicate that once this duty cycle is increased, the sensed parameters are closer to but not within the target values. In this situation, the device update module 71 continues to issue instructions that cause the IDC processor 62 to generate commands to increase the duty cycle of this current source 120. However, as a result of the increase of the on duty cycle of the source, the data generated in step 286 may indicate that the sensed parameters have moved further away from the target values. In this situation, the device update module 71 generates instructions that cause the source being adjusted to decrease the on duty cycle. The loop back from step 286 to step 282 represents this resetting of the component values until the sensed parameters are within the range specified by the target values.

Ideally, after some adjustment of the component values, it is determined in step 286 that the sensed parameters are within the range specified by the target values. Once the IDC processor parameter compare module 73 makes this determination, the processor branches to step 278. The processor 62 continues to cause the electrodes 106 or 162 integral with the current flowing arrays to flow current in accordance with the new values. This continues until as a result of the analyses of steps 274 and 276 it is determined the condition of the patient has changed it is necessary to again adjust the current flows.

System 30 of this invention does more than flow current through selected portions of an individual's tissue in order to provide a therapy. System 30 is constructed so that a single control unit, the implantable control device 32, regulates the operation of a number of spaced apart electrode arrays 36 and 38. The IDC 32 generates command blocks 184 based on parameters that sensed by other devices, array 40 for example, separate from the arrays 36 and 38 through which the current is flowed. Thus, system 30 is an integrated system that simultaneously provides therapeutic current flows at different locations within the patient if such flows are useful in treating the patient's condition.

Bus 32 of this invention functions as the communications path by which power, command and data signals are transmitted to/from the IDC 32 and the other devices of the system. The distance between the wire 88 of the bus trunk 84 and the coils 146 integral with the bus branches 144 is less than 1.0 mm and often 0.5 mm or less. This makes it unlikely that there will be a failure in the inductive signal exchange between the bus trunk 84 and bus branches 144.

System 30 is also able to adjust to changes in the state of the patient. One way by which the system adjusts to the changes of the patient is that the cuffs 152 integral with the bus branches 144 are able to move over the bus trunk 84. This means that the bus branches 144 themselves are able to move relative to the bus trunk 84. This adjustable relationship is beneficial because, how tissue or organs seat with the patient can change. Such tissue or organ movement can be the result of the normal movements of day-to-day living or the result of an unusual activity such as the body being exposed to a mechanical shock. This changing of the position of the tissue or organ can displace a portion of the bus trunk 84 or bus branch 144 next to the tissue or organ. However, since location of the trunk-to-branch connection can change, the displacement of the trunk 84 or branch 144 relative to the other of the branch or trunk does not result on a significant tension being placed on these bus components. By reducing this tension, especially in the bus branches 144, the likelihood that a branch will pull the attached array or other device away from its deployed position or separating from the device is substantially eliminated.

Further, system 30 is designed so to monitor changes in the state of the patient. Based on these changes, the system adjusts the therapy provided to the patient. This is useful in the event changes in the state of the patient, for example from sitting to walking and then back again to sitting, cause changes in the state of the patient's tissue that warrant changes in the therapy applied to the patient. Changes in the condition of the patient's tissue, such as scaring of the dura over the patient's spinal cord may also warrant such changes in the therapy provided to the patient.

The foregoing is limited to one specific version of the system 30 of this invention for providing therapy to a patient. Other versions of the system 30 of this invention may be possible. For example, while bus 34 is described and illustrated as having a single bus trunk 84 and plural bus branches 144. In some versions of the invention there may be a single array or other device connected to the IDC 32. Still, to ensure the connection between the IDC and the array, the bus arrangement comprising the bus trunk-to-bus branch construction of this invention may be desirable even though there is only a single bus branch 144.

In some constructions of this invention, the system may consist of an IDC 32 and two arrays 36. It should be appreciated that the constructions of the devices of this invention: the IDC; array 36; array 38; and array 40 are not intended to be limiting. The devices of this invention may have constructions different from what is described. For example, some attached devices may include only a single electrode. Some electrode arrays may only have on-array components through which current can be sourced or sunk. These arrays may not have any components capable of providing signals indicating the levels present at their electrodes.

An alternative electrode array incorporated into system 30 is constructed so that, integral with each electrode is an application specific integrated circuit (ASIC). Each ASIC includes circuits for sourcing and/or sinking current through the electrode. The ASIC also includes a control circuit with a unique address. By providing each electrode with its own ASIC the need to provide the drive module that sources/sinks current from/to the plurality of electrodes is eliminated. One such construction of this electrode array is disclosed in the Applicant's incorporated by reference U.S. Pat. Pub. No. 2011/0034977 A1. When this type of electrode array is incorporated into system 30, the IDC processor-generated commands may only contain the addresses of the individual ASICs; there may not be a need to provide the commands with addresses of the array.

Alternatively, in some embodiments of system 30 wherein a uniquely addressable ASIC is integral with each electrode, it may still be necessary to provide an array address. These data may be necessary if the array also includes a router that forwards the commands intended for the associated on-array ASICs to the designated ASICs.

Thus, both the number of devices forming the system as well as the individual structure of the devices may vary from what has been described. Similarly, in some constructions of this invention, the system may consist of an IDC 32 and two arrays 36. Accordingly not only can the constructions of the individual devices vary from what has been described, so can the number of devices.

Also while system 30 is shown as having a single bus 34, it should be understood that this for illustrative and not limiting. In alternative versions of the invention, plural buses may extend from the IDC 32. One or more these buses may connect the IDC to plural devices. Still on or more of the buses may not even be a bus in the sense that plural devices are connected to it. These single IDC-to-single device connections may be necessary if the nature of the power or bandwidth requirements of the device is such is that it would be difficult with the device to share a bus with other devices.

Also, while in many versions of the system there will be a single IDC 32, this is not a limiting feature of this invention. Some versions of the invention may include plural IDCs. Each IDC may be implanted adjacent the one or more arrays or other devices it controls. A bus connects the IDCs. In this version of the invention, each IDC powers and regulates the arrays or other devices to which it is connected. The IDCs exchange information and commands to operate all the arrays and devices as an integrated system.

Likewise, there may be reasons to provide versions wherein the bus trunk does not extend from the IDC 32. In these versions of the invention, the bus trunk may extend from one of the devices controlled by or monitored by the IDC 32. A branch line extends from the IDC 32. The branch line includes the cuff that is disposed over and capable of moving relative to the bus. In these versions of the invention it should be understood that signals output by the IDC are initially output over the branch line that extends from the IDC. These signals are inductively transferred to the trunk. From the trunk the signals are applied to the device to which the trunk is connected. If there are other branch lines attached to the trunk, these signals are also inductively transferred to these branch lines. From, these branch lines the signals are applied to the device from which these branch lines extend.

It should similarly be recognized that there is no requirement that in all versions of the invention the cuffs associated with the bus branch lines extend completely around the trunk. For example in some versions of the invention it may be desirable to provide branch lines with cuffs that are C-shaped. This arrangement allows the cuffs to be slip fitted around the bus trunk. This arrangement could make it possible to, post implantation of the components forming the system connect the branch lines to or disconnect the branch lines from the trunk bus.

In some versions of the invention, the device for providing therapy to the patient may not be an array that sources and/or sinks current. One type of alternative device may be a module that includes a reservoir with a small pump. Based on signals generated by the IDC 32, the pump is selectively actuated to pump the therapeutic agent disposed in the reservoir to the surrounding tissue. Alternatively, the therapeutic device may include some type of moving member such as a piezoelectric member. Based on the signals from the IDC this member is actuated in order to vibrate against the tissue adjacent the device.

Similarly, some devices implanted in the patient may in addition to controlling and powering other devices have additional functions. These device controllers may include sensors for monitoring the physiological state of the adjacent tissue. Based full or in part on this monitoring, the device sends regulates the operation of the remotely implanted therapeutic devices. Alternatively, a device controller may include components able to provide therapy. Based on the signals received from the remotely implanted therapeutic devices, this devices regulates the operation of its internal therapy providing components.

Likewise, the described protocol in which signals are exchanged over bus 34 should similarly be understood to be illustrative and not limiting. In some versions of the invention for example, when an array or device has data it wants to transmit to the IDC 32, the array/device must request a time slot for transmitting the data. The IDC assigns the time slot. Then, the array (device) transmits the data in the designated time slot. Similarly, data may be exchanged between the system devices during preassigned time slot. For example, the protocol may be such that, in each time frame data are transmitted from/to the IDC to/from a specific device. Transmitting data in accordance with this protocol eliminates the need to provide a command with a block that identifies the device to which that command is intended and the processing of that command. The format of the command blocks 184 as well as the blocks in which the data transmitted from the devices to the IC 32 is a function of the protocol under which the signals carrying these data are exchanged.

It should also be understood that the method of assembling the components forming the system and the method of implantation may vary from what has been described. Thus, it may be desirable to, implant one or more of the components of the system prior to connecting the components to the bus. Only after these components are implanted are they connected to the bus trunk.

Accordingly, it is an object of the appended claims to cover all variations and modifications that come within the true spirit and scope of the invention.

What is claimed is:

1. An implantable system for providing therapy to or monitoring the physiology of a living being, said system including: a plurality of devices each of which is implantable in the living being, wherein the devices are separate from and spaced apart from each other wherein:
    there is at least one first device that, when actuated, applies therapy and/or measures a physiological state of tissue against which the device is implanted;
    and there is at least one a second device separate from the at least one first device for generating commands to the at least one first device or receiving data signals from the at least one first device;
    a trunk with at least one conductor extends from said at least one first device or from said at least one second device;
    and a branch with at least one conductor extends from said at least one second device or said at least one first device, said branch including a cuff with an extension of the at least one branch conductor, said cuff being disposed at least partially around said trunk and being slip fitted over said trunk so as to be, post implantation of the system, able to independently move over said trunk; and
    wherein, said device from which said trunk extends outputs or receives AC signals over the at least one trunk conductor so that the signals are inductively exchanged between the at least one trunk conductor and the at least one branch conductor so as to result in signal exchange between the said devices to which said trunk and said at least one branch are connected.

2. The implantable system of claim 1, wherein said trunk includes a non-conductive shell in which the at least one trunk conductor is embedded.

3. The implantable system of claim 1, wherein there are at least three implantable devices; said trunk extends from one of said implantable devices; a branch with a cuff extends from other said implantable devices wherein said cuffs are attached to said trunk at separate locations along said trunk and each said cuff is able to move over said trunk.

4. The implantable system of claim 1, wherein said first device is configured to operate in response to externally generated commands; said second device is configured to transmit commands to said first device to control operation of said first device; said trunk extends from said second device; and said branch with said cuff extends from said first device.

5. The implantable system of claim 4, wherein said second device is further configured to: receive over said trunk signals representative of a physiological state monitored by at least one of said first implantable devices; and in response to the signals representative of the monitored physiological state, outputs command signals to the said first device that is responsive to the externally generated commands.

6. The implantable system of claim 1, wherein the at least one first device receives command signals from the at least one second device over said trunk and said branch and the at least one first device includes a power harvesting circuit able to store charge in signals received from the at least one second device over said trunk and said branch.

7. The implantable system of claim 1, wherein said cuff extends completely circumferentially around said trunk.

8. The implantable system of claim 1, wherein two conductors are disposed in said trunk.

9. The implantable system of claim 8, wherein said trunk includes: a core of flexible material, wherein one of the conductors extends through the core and a second conductor of the two conductors is disposed over the core; and a shell disposed over said core and the conductor disposed over the core.

10. The implantable system of claim 1, wherein said branch includes two conductors.

11. An implantable system for providing therapy to or monitoring physiology of a living being, said system including: a first implantable device, said first implantable device including: a first structural support component designed for implantation into a living being; at least one component mounted to or in said first structural support component for performing at least one of: providing therapy to living tissue; or monitoring the physiology of the living tissue;
    a first sleeve containing at least one wire that extends from the first structural support component;
    a first cuff attached to said first sleeve at a location space from said first structural support component, said first cuff including a coil disposed therein that is connected to said first sleeve wire;
    a second implantable device, said second implantable device including:
a second structural support component designed for implantation into the living being, said second structural component being separate from said first structural component;
    at least one component mounted to or in said second structural support component for performing at least one of: controlling said components of said first implantable device; receiving data from said first implantable device; providing power to said first implantable device; providing therapy to the living being; or monitoring the physiology of the living being;
    a second sleeve containing at least one wire that extends from said second structural support component, said second sleeve being separate from said first sleeve;

a second cuff attached to said second sleeve at a location spaced from the structural support component, said cuff including a coil disposed therein that is connected to said second sleeve wire;

a transmitting unit internal to at least one of said first implantable device or said second implantable device for transmitting AC signals over the said sleeve wire and said cuff coil associated with said device and a receiving unit internal to at least one of the other of said second implantable device or said first implantable device for receiving from said cuff coil and said sleeve wire associated with said device AC signals; and a trunk containing at least one wire, said trunk being designed for implantation into the living being wherein both said first cuff and said second cuff are slip fitted over said trunk so that said cuffs are, post implantation of said system, able to independently move over said trunk and so that the said coil internal to each said cuff is able to inductively exchange signals with said trunk wire so that AC signals applied to one said cuff coil are inductively transferred to said trunk wire and from said trunk wire are inductively transferred to the other said cuff coil.

12. The implantable system of claim 11, wherein at least one said cuff extends completely circumferentially around said trunk.

13. The implantable system of claim 11, wherein said trunk includes: a core of flexible material, a first wire that extends through said core; a second wire that is disposed over said core and connected to the first said wire; and a shell disposed over said core and the conductor disposed over the core.

14. The implantable system of claim 11, wherein said at least one component of said first implantable device is an electrode for performing at least one from the group consisting of: sourcing current to tissue; sinking current from tissue; and monitoring a potential across tissue.

15. The implantable system of claim 11, wherein said at least one component of said first implantable device includes at least one from the group consisting of: a reservoir for holding a therapeutic agent that is infused into tissue; and a moving member that provides a therapeutic effect.

16. The implantable system of claim 11, wherein at least one of said implantable devices further includes a power harvesting circuit able to store a charge in signals received over the cuff coil associated with said implantable device and that distributes the charge to other components integral with said implantable device.

17. The implantable system of claim 11, wherein components of said first implantable device perform therapy on the living being and said components perform therapy in response to externally generated command signals; and said components of said second implantable are configured to: receive over the said second cuff coil and said second sleeve wire, signals representative of physiological state of the living being; and in response to the signals representative of the monitored physiological state, output command signals over said second sleeve wire, said second cuff coil and said trunk wire to the said components of said first implantable device that result in the performance of therapy by said components of said first implantable device.

18. The implantable system of claim 11, further including a third implantable device, said third implantable device including:

a third structural support component designed for implantation into the living being, said third structural component being separate from said first structural component and said second structural component; and at least one component mounted to or in said third structural component for performing at least one of: providing therapy to the living being; monitoring the physiology of the living being; controlling operation of at least one of the first or second implantable devices; receiving data from at least one of the first or second implantable devices; and providing power to either the first or second implantable devices; and wherein said trunk is connected to and extends from said third structural support component and said at least one wire of said trunk is connected to said at least one component of said third implantable device.

19. The implantable system of claim 11, wherein said coil of at least one said cuff is wound in a helix.

* * * * *